US011628238B2

(12) United States Patent
Liu et al.

(10) Patent No.: US 11,628,238 B2
(45) Date of Patent: Apr. 18, 2023

(54) COMPOSITE MEMBRANE COMPRISING A DECELLULARIZED AMNIOTIC MEMBRANE AND A METHOD FOR PREPARING THE SAME

(71) Applicants: WUHAN KANGCHUANG TECHNOLOGY CO., LTD., Hubei (CN); THE JOHNS HOPKINS UNIVERSITY, Baltimore, MD (US)

(72) Inventors: Huanhuan Liu, Baltimore, MD (US); Juan Wu, Wuhan (CN); Brian Ginn, Baltimore, MD (US); Haiquan Mao, Baltimore, MD (US)

(73) Assignees: THE JOHNS HOPKINS UNIVERSITY, Baltimore, MD (US); WUHAN KANGCHUANG TECHNOLOGY CO., LTD., Hubei (CN)

( * ) Notice: Subject to any disclaimer, the term of this patent is extended or adjusted under 35 U.S.C. 154(b) by 451 days.

(21) Appl. No.: 16/629,419

(22) PCT Filed: Jul. 14, 2017

(86) PCT No.: PCT/US2017/042164
§ 371 (c)(1),
(2) Date: Jan. 8, 2020

(87) PCT Pub. No.: WO2019/013822
PCT Pub. Date: Jan. 17, 2019

(65) Prior Publication Data
US 2020/0179566 A1   Jun. 11, 2020

(51) Int. Cl.
*A61L 27/36*   (2006.01)
*A61L 27/18*   (2006.01)
*A61L 27/44*   (2006.01)
*A61L 27/52*   (2006.01)
*A61L 27/58*   (2006.01)
*C08L 67/04*   (2006.01)

(52) U.S. Cl.
CPC ........... *A61L 27/3604* (2013.01); *A61L 27/18* (2013.01); *A61L 27/3691* (2013.01); *A61L 27/44* (2013.01); *A61L 27/52* (2013.01); *A61L 27/58* (2013.01); *C08L 67/04* (2013.01); *A61L 2400/12* (2013.01); *A61L 2430/34* (2013.01); *A61L 2430/40* (2013.01)

(58) Field of Classification Search
CPC ...... A61L 27/3604; A61L 27/52; A61K 35/50
See application file for complete search history.

(56) References Cited

U.S. PATENT DOCUMENTS

| | | | |
|---|---|---|---|
| 2014/0079759 A1 | 3/2014 | Patel et al. | |
| 2014/0227336 A1 | 8/2014 | Guilak et al. | |
| 2014/0342015 A1* | 11/2014 | Murphy | A61K 35/50 435/268 |

FOREIGN PATENT DOCUMENTS

| | | |
|---|---|---|
| CA | 2925688 C | 10/2019 |
| EP | 2646065 A4 | 3/2016 |

OTHER PUBLICATIONS

Wilshaw, S-P. et al. "Production of an Acellular Amniotic Membrane Matrix for Use in Tissue Engineering" Tissue Engineering, 2006, 12 (8), pp. 2117-2129 (Year: 2006).*
PCT International Search Report for PCT/US17/42164 dated Oct. 13, 2017.
Wilshaw, et al., "Production of an Acellular Amniotic Membrane Matrix for Use in Tissue Engineering," Tissue Engineering, 12(8):1-13 (2006).
Teh, et al., "Tissue Engineering of the Tympanic Membrane," Tissue Engineering, B. Reviews, 19(2):116-132 (2013).

* cited by examiner

*Primary Examiner* — Andrew S Rosenthal
(74) *Attorney, Agent, or Firm* — Polsinelli PC

(57) ABSTRACT

The present invention relates to the field of biomedical technology, and relates to a composite membrane comprising a decellularized amniotic membrane, a use of the composite membrane, and a method for preparing the composite membrane.

19 Claims, 10 Drawing Sheets

Surface modification    +      +      −

Compression          +      −      +

COMPOSITE MEMBRANE COMPRISING A DECELLULARIZED AMNIOTIC MEMBRANE AND A METHOD FOR PREPARING THE SAME

CROSS REFERENCE TO RELATED APPLICATIONS

The present application is the U.S. National Phase under 35 U.S.C. § 371 of International Application No. PCT/US2017/042164, filed Jul. 14, 2017, with the invention title of "A composite membrane comprising a decellularized amniotic membrane and a method for preparing the same", the entire content of which is herein incorporated by reference.

TECHNICAL FIELD

The present invention relates to the field of biomedical technology, and relates to a composite membrane comprising a decellularized amniotic membrane, a use of the composite membrane and a method for preparing the composite membrane.

BACKGROUND ART

Amniotic membrane (AM) locates in the inner layer of placenta, is translucent, with soft texture, rich in a variety of growth factors and cytokines, and has been used in various clinical applications and animal studies for treatment and regeneration of soft tissues, such as in skin transplantation, ocular surface reconstruction, and treatment of diabetic ulcers, etc. The repair effects of amniotic membranes are mainly achieved via release of related factors, inhibition of inflammatory responses, promotion of re-epithelialization, inhibition of fibrosis and reduction of scar formation. Recent studies have shown that amniotic membranes can regulate inflammatory environment, promote transformation of M1 type macrophages to M2 type macrophages, inhibit inflammatory response, and promote regeneration. These characteristics indicate that amniotic membranes are ideal tissue engineering materials for soft tissue repair.

The bioactivity and structure of amniotic membrane are best preserved in a freshly prepared amniotic membrane, but the high cost associated with the preservation and delivery of fresh amniotic membrane prevents its wide-spread use. The existing methods for preservation of amniotic membranes mainly include wet preservation and lyophilization preservation. At present, the wet-preserved amniotic products include AmnioGraft®, NEOX®, etc. Lyophilized amniotic membranes have reduced the cost for preservation and transportation, but they are poor in mechanical properties and fragile. Recently, many researchers try to improve stability, mechanical properties and handleability of amniotic membranes by using chemical or enzymatic cross-linkers. However, these methods provide limited improvement, and may result in significant loss of some bioactive matters in amniotic membranes during the processing, and the introduced chemicals may potentially reduce the biocompatibility of amniotic membranes. Other alternative approaches rely on amniotic extracts or using amniotic extracts in hydrogel forms. These approaches retain active substances of amniotic membranes to a certain extent, but completely destroy the natural structure of amniotic membrane, which has been confirmed to promote re-epithelialization.

Contents of the Invention

In the present invention, the scientific and technical terms used herein have the same meaning as commonly understood by one of ordinary skill in the art, unless otherwise indicated. Also, the laboratory steps involved in the text are conventional steps that are widely used in the corresponding fields. Meanwhile, for the purpose of better understanding the present invention, definitions and explanations of related terms are provided below.

The amniotic membrane of the present invention is the innermost layer of placenta and is a transparent and ductile tissue, free of nerve, blood vessel and lymphatic vessel. The natural amniotic membrane consists of an epithelial cell layer, a basement membrane, a stromal layer, a fibroblast layer and a sponge layer. The natural amniotic membrane can be divided into two sides, one is epithelial side with epithelial cell layer (the side with basement membrane after removal of epithelial cell layer), and the other is stromal side, i.e., the side with sponge layer. By removing epithelial cell layer from a natural amniotic membrane, a de-epithelialized amniotic membrane can be obtained, which consists of a basement membrane, a stromal layer, a fibroblast layer and a sponge layer; or by removing epithelial cell layer and fibroblast layer, a fully decellularized amniotic membrane is obtained, which consists of a basement membrane, a stromal layer and a sponge layer. The decellularized amniotic membrane (dAM) of the present invention comprises the de-epithelialized amniotic membrane and the fully decellularized amniotic membrane, wherein the stromal side of the decellularized amniotic membrane is the side of the decellularized amniotic membrane, which has a sponge layer.

As used herein, the term "electrospinning", also known as "electrostatic spinning", refers to a process of forming fibers using a polymer solution or melt under the action of a high voltage electric field, comprising allowing the polymer solution or melt with charges to flow and deform in the electric field, then solidifying the polymer solution or melt jet by solvent evaporation or melt cooling to obtain fibers. Electrospinning can be used to obtain nanofibers or microfibers. Electrospinning devices typically include a high voltage power supply, a solution storage device, an injection device, and a collection device. In a conventional collection mode, fibers are scattered in a random manner on a collection device and exist in a form of nonwoven; while by using a specific collection mode, fibers that are parallel to fiber axis to a certain extent could be obtained.

As used herein, the term "fiber" refers to a relatively flexible, relatively homogeneous object having a high ratio of length to width (e.g., greater than 100), wherein the width refers to a diameter of a cross-section perpendicular to its length. The cross-section of fiber may be of any shape, such as circular or non-circular shape. In the case of the fibers with non-circular cross-section, the term "diameter" refers to the largest cross-sectional dimension.

As used herein, the term "nanofiber" in a general sense refers to a fiber having a diameter of less than about 5000 nm, less than about 1000 nm, less than about 800 nm, less than about 500 nm, or less than about 100 µm. The term "microfiber" refers to a fiber having a diameter of less than about 100 µm, less than about 80 µm, less than about 50 µm or less than about 10 µm. The nanofiber or microfiber may be hollow, or ribbon-like fibers flattened along their longitudinal cross-sectional direction.

The "fibrous layer" described in the present invention is mainly composed of fibers and may contain other substances (e.g., nutrients, extracellular matrix, cytokines and/or pharmaceutically active ingredients), in which the fibers may be raxidomly distributed or, to a certain extent, distributed in a parallel manner. The fibers can be intertwined or overlapped with each other.

As used herein, the term "nanofiber layer" refers to a fibrous layer comprised of a large proportion of nanofibers. The large proportion means that, for example, as to a nanofiber layer, more than about 50%, such as more than about 60%, about 70%, about 80%, about 90%, of the fibers in the fibrous layer are nanofibers, or even about 100% of the fibers in the fibrous layer are nanofibers.

As used herein, the term "microfiber layer" refers to a fibrous layer comprised of a large proportion of microfibers. The large proportion means that, for example, as to a microfiber layer, more than about 50%, such as more than about 60%, about 70%, about 80%, about 90%, of the fibers in the fibrous layer are microfibers, or even about 100% of the fibers in the fibrous layer are nanofibers.

As used herein, the term "nonwoven" refers to a web comprising substantially randomly oriented fibers, in which the overall repeating structure in fiber arrangement cannot be distinguished by the naked eye. The fibers may be bonded to each other, or may be non-bonded, and entangled or lapped to impart strength and integrity to the web. The fibers constituting the nonwoven may be short fibers or continuous fibers, and may comprise a single material or more than one materials, or may be a combination of different fibers or a combination of similar fibers each comprising a different material.

As used herein, the term "nanofiber membrane" refers to a membrane essentially composed of nanofibers. As used herein, the term "microfiber membrane" refers to a membrane essentially composed of microfibers. In the nanofiber membrane or microfiber membrane, the fibers are arranged in a random manner, or to a certain extent in parallel to each other, and the fibers can overlap. The nanofiber membrane or microfiber membrane has a pore that can be used for permeation. A common method for forming the nanofiber membrane or microfiber membranes is electrospinning method, and other possible methods are thermally induced phase separation method, self-assembly method, template method, etc., which can be seen in: 1) Carlos A; et al. Scaffolds for Tissue Engineering Via Thermally induced Phase Separation, Advances in Regenerative Medicine. ISBN 978-953-307-732-1; 2) Martin, C; (1995). Template synthesis of electronically conductive polymer nanostructures. Ace Chem Res. 1995, 28 (2): 61-68. Doi: 10.1021/ar00050a002; 3) Zhang, C; et al. (2014). "Self-assembled peptide nanofibers designed for biological enzymes for catalyzing ester hydrolysis" (11): 15-23. Doi: 10.1021/nn5051344. PMID 25375351.

As used herein, the term "polymer" refers to a natural or synthetic organic compound having a high molecular weight (e.g., greater than 1000) of which the structure can be represented by a repeating unit, including homopolymers and copolymers. Synthetic polymers are typically formed by monomer addition or monomer polycondensation.

As used herein, the term "homopolymer" refers to a polymer formed from a single repeating unit (monomer residue).

As used herein, the term "copolymer" refers to a polymer formed from two or more different repeating units (monomer residues), including, but not limited to, alternating copolymers, random copolymers, block copolymer and grafted copolymers.

As used herein, "biocompatibility" means that a material (and its possible degradation product) is non-toxic to cell, and is compatible with a host after being implanted to the host (e.g., human body), without inducing significant or serious side effects, for example, without causing toxic effects on the host (e.g., human tissue), without causing immune rejection, allergic reactions, or inflammatory responses in the host.

As used herein, "biodegradability" means that a material can be degraded and absorbed by a cell or organism and that its degradation product is biocompatible.

As used in this specification and the appended claims, the singular forms "a", "an", as well as "the/said" include plural referents, unless the context clearly dictates otherwise.

As used herein, the term "about" should he understood by those skilled in the art and will vary to some extent by the context in which it is used. The term of "about" would mean that having a deviation no more than ±10% of a particular value or range, if its meaning is not clear to the person skilled in the art, depending on the context in which the term is applied.

As used herein, the term "treatment" refers to a condition that heals or at least partially prevents the progress of a disease, or relieves a disease.

In order to solve the problems in the prior art, the inventors of the present application have composited a decellularized amniotic membrane with a polymer fiber product to obtain a composite membrane comprising the decellularized amniotic membrane and the polymer fiber layer. The composite membrane of the present invention is easy to store and has better mechanical properties and operability than native amniotic membranes, thereby providing the following invention:

In one aspect, the present invention provides a composite membrane comprising at least one decellularized amniotic membrane and at least one fibrous layer containing a polymer fiber, in which the fibrous layer is attached to the decellularized amniotic membrane.

In certain embodiments, the fibrous layer is attached to a stromal side of the decellularized amniotic membrane.

In certain embodiments, the fibrous layer is attached directly to the decellularized amniotic membrane. Preferably, there is not an added adhesive layer or a substance having adhesive effect between the fibrous layer and the decellularized amniotic membrane.

In certain embodiments, the fibrous layer is attached to the decellularized amniotic membrane by a chemical bond.

In certain embodiments, the fibrous layer is a nanofiber layer or a microfiber layer.

In some embodiments, the composite membrane has a thickness of 30 μm to 500 μm, for example 30 μm to 100 μm, 100 μm to 200 μm, 200 μm to 300 μm, 300 μm to 400 μm or 400 μm to 500 μm, for example 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, or 500 μm.

In some embodiments, the fibrous layer has a thickness of 10 μm to 300 μm, for example 10 μm to 100 μm, 100 μm to 200 μm or 200 μm to 300 μm, for example 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm or 300 μm.

In some embodiments, the polymer fibers have an average diameter of 200 μm to 5 μm, for example 200 nm to 500 mm, 500 mm to 1 μm, 1 μm to 2 μm, 2 μm to 3 μm, 3 μm to 4

μm or 4 μm to 5 μm, for example 200 nm, 300 nm, 400 nm, 500 nm, 600 nm, 700 nm, 800 nm, 900 nm, 1 μm, 1.1 μm, 1.2 μm, 1.3 μm, 1.4 μm, 1.5 μm, 1.6 μm, 1.7 μm, 1.8 μm, 1.9 μm, 2 μm, 2.1 μm, 2.2 μm, 2.3 μm, 2.4 μm, 2.5 μm, 2.6 μm, 2.7 μm, 2.8 μm, 2.9 μm, 3 μm, 3.1 μm, 3.2 μm, 3.3 μm, 3.4 μm, 3.5 μm, 3.6 μm, 3.7 μm, 3.8 μm, 3.9 μm, 4 μm, 4.1 μm, 4.2 μm, 4.3 μm, 4.4 μm, 4.5 μm, 4.6 μm, 4.7 μm, 4.8 μm, 4.9 μm or 5 μm.

In the composite membrane of the present invention, the fibrous layer has a pore for facilitating transportation of substances. In some embodiments, the fibrous layer has a porosity of 50% to 95%, for example 50% to 55%, 55% to 60%, 60% to 65%, 65% to 70%, 70% to 75%, 75% to 80%, 80% to 85%, 85% to 90% or 90% to 95%, for example 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 97%, 93%, 94% or 95%.

In some embodiments, the fibrous layer has a specific surface area of 2 $m^2/g$ to 40 $m^2/g$, for example 2 $m^2/g$ to 10 $m^2/g$, 10 $m^2/g$ to 20 $m^2/g$, 20 $m^2/g$ to 30 $m^2/g$ or 30 $m^2/g$ to 40 $m^2/g$, for example 2 $m^2/g$, 3 $m^2/g$, 4 $m^2/g$, 5 $m^2/g$, 6 $m^2/g$, 7 $m^2/g$, 8 $m^2/g$, 9 $m^2/g$, 10 $m^2/g$, 11 $m^2/g$, 12 $m^2/g$, 13 $m^2/g$, 14 $m^2/g$, 15 $m^2/g$, 16 $m^2/g$, 17 $m^2/g$, 18 $m^2/g$, 19 $m^2/g$, 20 $m^2/g$, 21 $m^2/g$, 22 $m^2/g$, 23 $m^2/g$, 24 $m^2/g$, 25 $m^2/g$, 26 $m^2/g$, 27 $m^2/g$, 28 $m^2/g$, 29 $m^2/g$, 30 $m^2/g$, 31 $m^2/g$, 32 $m^2/g$, 33 $m^2/g$, 34 $m^2/g$, 35 $m^2/g$, 36 $m^2/g$, 37 $m^2/g$, 38 $m^2/g$, 39 $m^2/g$ or 40 $m^2/g$.

In some embodiments, the polymer fiber is obtainable by electrospinning.

In some embodiments, the decellularized amniotic membrane is deepithelialized amniotic membrane or fully decellularized amniotic membrane.

In some embodiments, the amniotic membrane used for preparing the decellularized amniotic membrane is freshly obtained. In some embodiments, the amniotic membrane used for preparing the decellularized amniotic membrane is derived from a bovine, an equine, a suidae, a canine, a feline, a rodent or a primate, for example, derived from a human.

In the composite membrane of the present invention, the polymer fibers are preferably made of a polymer having biocompatibility and/or biodegradability.

In some embodiments, the polymer is a synthetic polymer, for example, selected from the group consisting of aliphatic polyesters, polyester ethers, polyphosphazenes, polycarbonates, polyamine acids, and any combination thereof, or, the polymer is a natural polymer, for example, selected from the group consisting of collagen, fibrin, chitosan, alginate, hyaluronic acid, fibronectin, gelatin, dextran, elastin, and any combination thereof.

In some embodiments, the polymer is selected from the group consisting of poly(lactic acid) (PLA) and copolymers thereof, polyglycolide (PGA) and copolymers thereof, polyhydroxyalkanoates (PHAs) and copolymers thereof, polycaprolactone (PCL) and copolymers thereof, fibronectin and collagen.

In some embodiments, the polymer is selected from the group consisting of polylactic acid) (PLA), polycaprolactone (PCL), polylactic acid-glycolate) copolymer (PLGA) and collagen.

In some embodiments, the polymer is capable of forming a hydrogel fiber. A polymer capable of forming a form hydrogel fiber (for example, collagen and fibronectin) can be electrospun to obtain a transparent fibrous layer that is suitable for repair of a transparent soft tissue (for example cornea).

In some embodiments, the fibrous layer is a PCL nanofiber layer, which has a structure similar to extracellular matrix, a high specific surface area, and a porous structure for facilitating cell migration and nutrient transportation. The PCL nanofiber layer is light and soft, can be attached to a surface of a tissue to be repaired, and has good tensile properties. In some embodiments, the PCL nanofiber layer has a thickness of 40 μm to 120 μm.

In some embodiments, the fibrous layer is a collagen fiber layer, which has good transparency and is suitable for repair of a transparent soft tissue (for example, cornea).

In the composite membrane of the present invention, the fibers in the fibrous layer can be present in various distributions, for example, are randomly distributed to form a structure similar to that of nonwoven, or arranged in parallel to a certain extent.

In some embodiments, the composite membrane of the present invention comprises at least two layers, wherein the fibers in each layer are arranged in parallel to a certain extent, in the present invention, "in parallel to a certain extent" means that the parallel angle of the fiber in the same layer is between 0° and 10°. In some embodiments, the fibers in different fibrous layers have different orientations. The superposition of fibers with different fiber orientations in different fibrous layers can optimize the mechanical properties of the composite membrane in various directions.

In some embodiments, the fibrous layer is directly attached to the decellularized amniotic membrane through a chemical bond (e.g., amido bond or ester bond). In some embodiments, the polymer fibers are provided with reactive groups. In some embodiments, the polymer fibers are provided with carboxyl groups. Preferably, the carboxyl groups on the polymer fibers are activated (for example, subjected to N-hydroxysuccinimide (NHS) activation). In some embodiments, the polymer fibers are provided with amino groups. Through the condensation reaction between carboxyl groups and amino groups, amido bonds are formed, which hind the fibrous layer and the decellularized amniotic membrane closely together. In some embodiments, the polymer fibers are provided with hydroxyl groups.

In the composite membrane of the invention, the polymer fiber plays a role as physical support, and the composite membrane has excellent mechanical properties.

In some embodiments, the composite membrane has a strain to failure of 5% to 200%, for example 5% to 50%, 50% to 100%, 100% to 150% or 150% to 200%, for example 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195% or 200%.

In some embodiments, the composite membrane has an elastic modulus of 0.2 MPa to 1000 MPa, for example 0.2 MPa to 10 MPa, 10 MPa to 50 MPa, 50 MPa to 100 MPa, 100 MPa to 200 MPa, 200 MPa to 300 MPa, 300 MPa to 400 MPa, 400 MPa to 500 MPa, 500 MPa to 600 MPa, 600 MPa to 700 MPa, 700 MPa to 800 MPa, 800 MPa to 900 MPa or 900 MPa to 1000 MPa, for example 0.2 MPa, 1 MPa, 10 MPa, 30 MPa, 501 MPa, 100 MPa, 120 MPa, 150 MPa, 180 MPa, 200 MPa, 230 MPa, 250 MPa, 280 MPa, 300 MPa, 350 MPa, 370 MPa, 400 MPa, 430 MPa, 460 MPa, 480 MPa, 500 MPa, 530 MPa, 550 MPa, 570 MPa, 600 MPa, 630 MPa, 660 MPa, 680 MPa, 700 MPa, 730 MPa, 750 MPa, 800 MPa, 830 MPa, 860 MPa, 880 MPa, 900 MPa, 930 MPa, 950 MPa or 1000 MPa.

In some embodiments, the composite membrane has a toughness of 0.5 $MJ/m^3$ to 50 $MJ/m^3$, for example 0.5

MJ/m³ to 1 MJ/m³, 1 MJ/m³ to 5 MJ/m³, 5 MJ/m³ to 10 MJ/m³, 10 MJ/m³ to 20 MJ/m³, 20 MJ/m³ to 30 MJ/m³, 30 MJ/m³ to 40 MJ/m³ or 40 MJ/m³ to 50 MJ/m³, for example 0.5 MJ/m³, 1 MJ/m³, 2 MJ/m³, 3 MJ/m³, 4 MJ/m³, 5 MJ/m³, 6 MJ/m³, 7 MJ/m³, 8 MJ/m³, 9 MJ/m³, 10 MJ/m³, 11 MJ/m³, 12 MJ/m³, 13 MJ/m³, 14 MJ/m³, 15 MJ/m³, 16 MJ/m³, 17 MJ/m³, 18 MJ/m³, 19 MJ/m³, 20 MJ/m³, 21 MJ/m³, 22 MJ/m³, 23 MJ/m³, 24 MJ/m³, 25 MJ/m³, 26 MJ/m³, 27 MJ/m³, 28 MJ/m³, 29 MJ/m³, 30 MJ/m³, 31 MJ/m³, 32 MJ/m³, 33 MJ/m³, 34 MJ/m³, 35 MJ/m³, 36 MJ/m³, 37 MJ/m³, 39 MJ/m³, 40 MJ/m³, 41 MJ/m³, 42 MJ/m³, 43 MJ/m³, 44 MJ/m³, 45 MJ/m³, 46 MJ/m³, 47 MJ/m³, 48 MJ/m³, 49 MJ/m³ or 50 MJ/m³.

In one aspect, the present invention provides a method for preparing a composite membrane comprising a decellularized amniotic membrane, comprising the steps of:

(1) providing a decellularized amniotic membrane;

(2) providing a polymer fiber sheet, in which at least one surface of the polymer fiber sheet has a reactive group;

(3) fitting the surface of the polymer fiber sheet that has the reactive group to the decellularized amniotic membrane.

In some embodiments, the method further comprises: freeze-drying the product of step (3).

In some embodiments, the decellularized amniotic membrane in step (1) is de-epithelialized amniotic membrane or fully decellularized amniotic membrane.

In some embodiments, the decellularized amniotic membrane in step (1) is prepared by a process comprising the steps of:

(1-1) treating the epithelial side of an amniotic membrane with a protease solution;

(1-2) washing the amniotic membrane with a buffer solution;

(1-3) removing epithelial cells from the amniotic membrane (e.g., scraping off epithelial cells from the amniotic membrane);

(1-4) washing the amniotic membrane with a buffer solution after removing the epithelial cells.

In some embodiments, the amniotic membrane in step (1-1) is freshly obtained.

In some embodiments, the amniotic membrane in step (1-1) is derived from a bovine, an equine, a suidae, a canine, a feline, a rodent or a primate, for example, derived from a human.

In some embodiments, the polymer fiber sheet in step (2) is a nonwoven, for example a nonwoven essentially composed of a nanofiber or a microfiber.

In some embodiments, the polymer fiber sheet is a nanofiber membrane or a microfiber membrane.

In some embodiments, the polymer fiber sheet is obtainable by electrospinning.

In some embodiments, the polymer fiber sheet has a thickness of 10 µm to 300 µm, for example 10 µm to 100 µm, 100 µm to 200 µm or 200 µm, to 300 µm, for example 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm or 300 µm.

In some embodiments, the fibers in the polymer fiber sheet have an average diameter of 200 nm to 5 µm, for example 200 nm to 500 nm, 500 nm to 1 µm, 1 µm to 2 µm, 2 µm to 3 µm, 3 µm to 4 µm or 4 µm to 5 µm, for example 200 nm, 300 nm, 400 nm, 500 nm, 600 nm, 700 nm, 800 nm, 900 nm, 1 µm, 1.1 µm, 1.2 µm, 1.3 µm, 1.4 µm, 1.5 µm, 1.6 µm, 1.7 µm, 1.8 µm, 1.9 µm, 2 µm, 2.1 µm, 2.2 µm, 2.3 µm, 2.4 µm, 2.5 µm, 2.6 µm, 2.7 µm, 2.8 µm, 2.9 µm, 3 µm, 3.1 µm, 3.2 µm, 3.3 µm, 3.4 µm, 3.5 µm, 3.6 µm, 3.7 µm, 3.8 µm, 3.9 µm, 4 µm, 4.1 µm, 4.2 µm, 4.3 µm, 4.4 µm, 4.5 µm, 4.6 µm, 4.7 µm, 4.8 µm, 4.9 µm or 5 µm.

In some embodiments, the polymer fiber sheet has a porosity of 50% to 95%, for example 50% to 55%, 55% to 60%, 60% to 65%, 65% to 70%, 70% to 75%, 75% to 80%, 80% to 85%. 85% to 90% or 90% to 95%, for example 50%, 51%, 52%, 53%, 54%, 55%, 56%, 57%, 58%, 59%, 60%, 61%. 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94% or 95%.

In some embodiments, the polymer fiber sheet has a specific surface area of 2 m²/g-40 m²/g, for example 2 m²/g to 10 m²/g, 10 m²/g to 20 m²/g, 20 m²/g to 30 m²/g or 30 m²/g to 40 m²/g, for example 2 m²/g, 3 m²/g, 4 m²/g, 5 m²/g, 6 m²/g, 7 m²/g, 8 m²/g, 10 m²/g, 11 m²/g, 12 m²/g, 13 m²/g, 14 m²/g, 15 m²/g, 16 m²/g, 17 m²/g, 18 m²/g, 19 m²/g, 20 m²/g, 21 m²/g, 22 m²/g, 23 m²/g, 24 m²/g, 25 m²/g, 26 m²/g, 27 m²/g, 28 m²/g, 29 m²/g, 30 m²/g, 31 m²/g, 32 m²/g, 33 m²/g, 34 m²/g, 35 m²/g, 36 m²/g, 37 m²/g, 38 m²/g, 39 m²/g or 40 m²/g.

In some embodiments, the polymer fiber is obtainable by electrospinning.

In some embodiments, the polymer fiber sheet is made of a polymer having biocompatibility and or biodegradability.

In some embodiments, the polymer is a synthetic polymer, for example, selected from the group consisting of aliphatic polyesters, polyester ethers, polyphosphazenes, polycarbonates, polyamino acids, and any combination thereof; or, the polymer is a natural polymer, for example, selected from the group consisting of collagen, fibrin, chitosan, alginate, hyaluronic acid, fibronectin, gelatin, dextran, elastin, and any combination thereof.

In some embodiments, the polymer is selected from the group consisting of polylactic; acid) (PLA) and copolymers thereof, polyglycolide (PGA) and copolymers thereof, polyhydroxyalkanoates (PHAs) and copolymers thereof, polycaprolactone (PCL) and copolymers thereof, fibronectin and collagen.

In some embodiments, the polymer is selected from the group consisting of poly(lactic acid) (PLA), polycaprolactone (PCL), poly(lactic acid-glycolide) copolymer (PLGA) and collagen.

In some embodiments, the polymer is capable of forming a hydrogel fiber. A polymer capable of forming a hydrogel fiber (for example, collagen and fibronectin) can be electrospun to obtain a transparent fibrous layer that is suitable for repair of a transparent soft tissue (for example cornea).

In some embodiments, the fibers in the polymer fiber sheet can be present in various distributions, for example, are randomly distributed, or arranged in parallel to a certain extent.

In some embodiments, the step (3) comprising: fitting the surface of the polymer fiber sheet that has the reactive group to the stromal side of the decellularized amniotic membrane.

In some embodiments, the polymer fiber sheet has a reactive group which is a carboxyl group. Preferably, the carboxyl group is an activated carboxyl group (for example, NHS activated carboxyl group). In some embodiments, the polymer fiber sheet has a reactive group which is an amino group. An amido bond can be formed via the condensation reaction between the carboxyl group and the amino group, so that the polymer fiber sheet and the decellularized amniotic membrane are bound closely. In some embodiments, the polymer fiber sheet has a reactive group which is a hydroxyl group.

In some embodiments, the fiber sheet has a reactive group in a concentration of 0.05 nmol/mm$^2$ to 5 nmol/mm$^2$, for example 0.05 nmol/mm$^2$ to 0.5 nmol/mm$^2$, 0.5 nmol/mm$^2$ to 1 nmol/mm$^2$, 1 nmol/mm$^2$ to 2 nmol/mm$^2$, 2 nmol/mm$^2$ to 3 nmol/mm$^2$, nmol/mm$^2$ to 4 nmol/mm$^2$ or 4 nmol/mm$^2$ to 5 nmol/mm$^2$, for example 0.05 nmol/mm$^2$, 0.1 nmol/mm$^2$, 0.2 nmol/mm$^2$, 0.3 nmol/mm$^2$, 0.4 nmol/mm$^2$, 0.5 nmol/mm$^2$, 0.6 nmol/mm$^2$, 0.7 nmol/mm$^2$, 0.8 nmol/mm$^2$, 0.9 nmol/mm$^2$, 1 nmol/mm$^2$, 1.1 nmol/mm$^2$, 1.2 nmol/mm$^2$, 1.3 nmol/mm$^2$, 1.4 nmol/mm$^2$, 1.5 nmol/mm$^2$, 1.6 nmol/mm$^2$, 1.7 nmol/mm$^2$, 1.8 nmol/mm$^2$, 1.9 nmol/mm$^2$, 2 nmol/mm$^2$, 2.1 nmol/mm$^3$, 2.2 nmol/mm$^2$, 2.3 nmol/mm$^2$, 2.4 nmol/mm$^2$, 2.5 nmol/mm$^2$, 2.6 nmol/mm$^2$, 2.7 nmol/mm$^2$, 2.8 nmol/mm$^2$, 2.9 nmol/mm$^2$, 3 nmol/mm$^2$, 3.1 nmol/mm$^2$, 3.2 nmol/mm$^2$, 3.3 nmol/mm$^2$, 3.4 nmol/mm$^2$, 3.5 nmol/mm$^2$, 3.6 nmol/mm$^2$, 3.7 nmol/mm$^2$, 3.8 nmol/mm$^2$, 3.9 nmol/mm$^2$, 4 nmol/mm$^2$, 4.1 nmol/mm$^2$, 4.2 nmol/mm$^2$, 4.3 nmol/mm$^2$, 4.4 nmol/mm$^2$, 4.5 nmol/mm$^2$, 4.6 nmol/mm$^2$, 4.7 nmol/mm$^2$, 4.8 nmol/mm$^2$, 4.9 nmol/mm$^2$ or 5 nmol/mm$^2$.

Preferably, step (3) is carried out at a suitable pressure and/or temperature to make the binding between the polymer fiber sheet and the decellularized amniotic membrane more closely.

In some embodiments, step (3) is carried out at a temperature of 4 to 25° C., for example 4° C. to 10° C., 10° C. to 15° C., 15° C.; to 20° C. or 20° C. to 25° C., for example 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. or 25° C.

In some embodiments, step (3) is carried out at a pressure of 1 to 10 MP, for example 1 MP, 2 MP, 3 MP, 4 MP, 5 MP, 6 MP, 7 MP, 8 MP, 9 MP or 10 MP.

In some embodiments, step (3) is carried out for 1 to 24 hours, for example 1 hour, 2 hours, 3 hours, 4 hours, 5 hours, 6 hours, 7 hours, 8 hours, 9 hours, 10 hours, 11 hours, 12 Hour, 13 hours, 14 hours, 15 hours, 16 hours, 17 hours, 18 hours, 19 hours, 20 hours, 21 hours, 22 hours, 23 hours or 24 hours.

FIG. 1 schematically shows a method for preparation of a composite membrane, comprising: treating a polymer fiber sheet (for example PCL nanofiber membrane) to carry a carboxyl group on its fiber; activating the carboxyl group; compressing the polymer fiber sheet with the activated carboxyl group together with a decellularized amniotic membrane to obtain a composite membrane.

In some embodiments, the method of the present invention further comprises: stacking at least two polymer fiber sheets. In some embodiments, the fibers in a polymer fiber sheet are arranged in parallel to a certain extent. In some embodiments, the parallel angle of the fiber in the same sheet is between 0° and 10°. In some embodiments, the fibers in different fibrous sheets have different orientations. The superposition of fibers with different fiber orientations in different fibrous sheets can optimize the mechanical properties of the composite membrane in various directions and improve the mechanical property of the composite membrane. FIG. 2 shows this process illustratively.

In one aspect, the present invention provides an article, comprising the composite membrane of the present invention. In some embodiments, the article comprising one or more layers of the composite membrane of the present invention. Preferably, the article of the present invention is used for repair of a damaged soft tissue (for example, skin, subcutaneous tissue, muscle, tendon, ligament, joint capsule, synovial sac, nerve, blood vessel, cornea) or for treatment of an ophthalmic disease. The article may be a dressing, a scaffold or a patch. The article may also be a substitute for a tissue or organ, for example an artificial skin or an artificial lumen.

In one aspect, the present invention provides a use of the composite membrane described above for the preparation of an article. Preferably, the article is used for repair of a damaged soft tissue (for example, skin, subcutaneous tissue muscle, tendon, ligament, joint capsule, synovial sac, nerve, blood vessel, cornea) or for treatment of an ophthalmic disease. The article may be a dressing, a scaffold or a patch. The article may also be a substitute for a tissue or organ, for example an artificial skin or an artificial lumen.

In one aspect, the present invention provides a method for repairing a damaged soft tissue (e.g., skin, subcutaneous tissue, muscle, tendon, ligament, joint capsule, synovial sac, nerve, blood vessel, cornea) of a subject, comprising administering the composite membrane or the article to the damaged soft tissue of the subject.

The present invention further provides a method for treatment of an ophthalmic disease in a subject, comprising administering the composite membrane or the article to an affected part in ocular region of the subject.

In some embodiments, the subject is a mammal, for example, a bovine, an equine, a suidae, a canine, a feline, a rodent, a primate; for example, the subject is a human.

Beneficial Technical Effects

The composite membrane of the invention has the advantages of both amniotic membrane and polymer fiber membrane, which retains the structure and biological function of an amniotic membrane, and also has the physical support function of the polymer fiber membrane. The composite membrane of the present application can be stored by freeze-drying to make ready-to-use products.

As compared with fresh or simply dehydrated amniotic membranes, the composite membrane of the present invention has good mechanical properties, is easy to operate, can be stored and transported at room temperature, reduces the cost of production, transportation and use, and therefore has a very good potential in applications. The composite membrane of the present invention can be used in a surgical operation, has good operability for a variety of operations including suturing, and will have a very wide range of applications in repair of a damaged soft tissue (for example, corneal injury, diabetic ulcers, arterial ulcers, lower extremity venous ulcers, or defects of tendons, muscles, or nerve tissue).

The method for preparing the composite membrane according to the present invention preserves the natural structure of stromal layer of amniotic membrane, and can make the decellularized amniotic membrane and the fibrous layer stably fit, so that the composite membrane has a stable integrated structure and excellent performance.

While the embodiments of the present invention will be described in detail with reference to the accompanying drawings and examples, it will be understood by those skilled in the art that the following drawings and examples are intended to be illustrative of the invention and are not intended to limit the scope of the invention. The various objects and advantageous aspects of the invention will become apparent to those skilled in the art from the following detailed description of the drawings and preferred embodiments.

BRIEF DESCRIPTION OF THE DRAWINGS

FIGS. 5a and 5d showed the surface morphologies of the amniotic membrane observed before and after decellularization under a normal optical microscope, respectively. FIGS. 5b and 5e were the results of observation of the amniotic membrane by a fluorescence microscope before and after decellularization, in which the dots in FIG. 5b are DAPI-stained nuclei, and no nucleus is observed in FIG. 5e. FIGS. 5c and 5f showed the surface morphologies of the amniotic membrane observed under the scanning electron microscope before and after decellularization.

FIGS. 18A-18C showed optical micrographs of the cross-sections after H&E staining, in which the scale bars were 20 μm. FIG. 18A showed that the natural amniotic membrane comprises a layer of epithelial cell and a sponge-like stromal structure. FIGS. 18B and 18C showed that the PCL nanofiber membrane (NF) merged into the stromal side of the decellularized amniotic membrane as observed on the cross-section of the composite membrane, and the amniotic membrane and the PCL nanofiber membrane were overlapped. FIGS. 18D to 18F were scanning electron micrographs of the cross-section, in which the scale bars were 10 μm, 2 μm, 1 μm in FIGS. 18D, 18E and 18F, respectively. The ultra-microstructure of the composite membrane showed that the PCL nanofiber membrane very closely bound to the decellularized amniotic membrane (FIGS. 18E, 18F). The location indicated by arrows showed that the decellularized amniotic membrane and PCL nanofiber membrane were tightly connected. The results showed that the PCL nanofiber membrane and the decellularized amniotic membrane successfully formed a composite membrane through physical and chemical interactions.

SPECIFIC MODES FOR CARRYING OUT THE INVENTION

While the embodiments of the present invention will be described in detail with reference to the following examples, it will be understood by those skilled in the art that the following examples are intended to be illustrative of the present invention and should not be construed as limiting the scope of the invention. When specific conditions were not given the examples, they were carried out in accordance with conventional conditions or the conditions recommended by the manufacturers. When the manufacturers of the used reagents or instruments were not indicated, they were all commercially available conventional products.

EXAMPLE 1

Preparation and Treatment of PCL Nanofiber Membrane

1. Preparation of PCL nanofiber membrane: A solution of 12 wt % polycaprolactone (PCL, MW 70 kDa, Sigma-Aldrich) was prepared. A certain amount PCL particles were weighed and dissolved in a solution of dichloromethane: methanol=4:1 at a final concentration of 12%. The PCL solution was added to a syringe, and a 27 G syringe needle was mounted. The entire syringe was placed on a motor-driven syringe pump, and was propelled with a voltage of 12 kV at an injection speed of 2.5 mL/h. A grounded tin foil paper was used to receive the ejected PCL nanofibers to form a nanofiber membrane with a membrane thickness of 80 μm, and the average diameter of the PCL nanofibers was 517 nm (517±178 nm).

According to the above process, the PCL nanofiber membranes with thicknesses of 40 μm, 80 μm and 120 μm were prepared.

Figure 1:
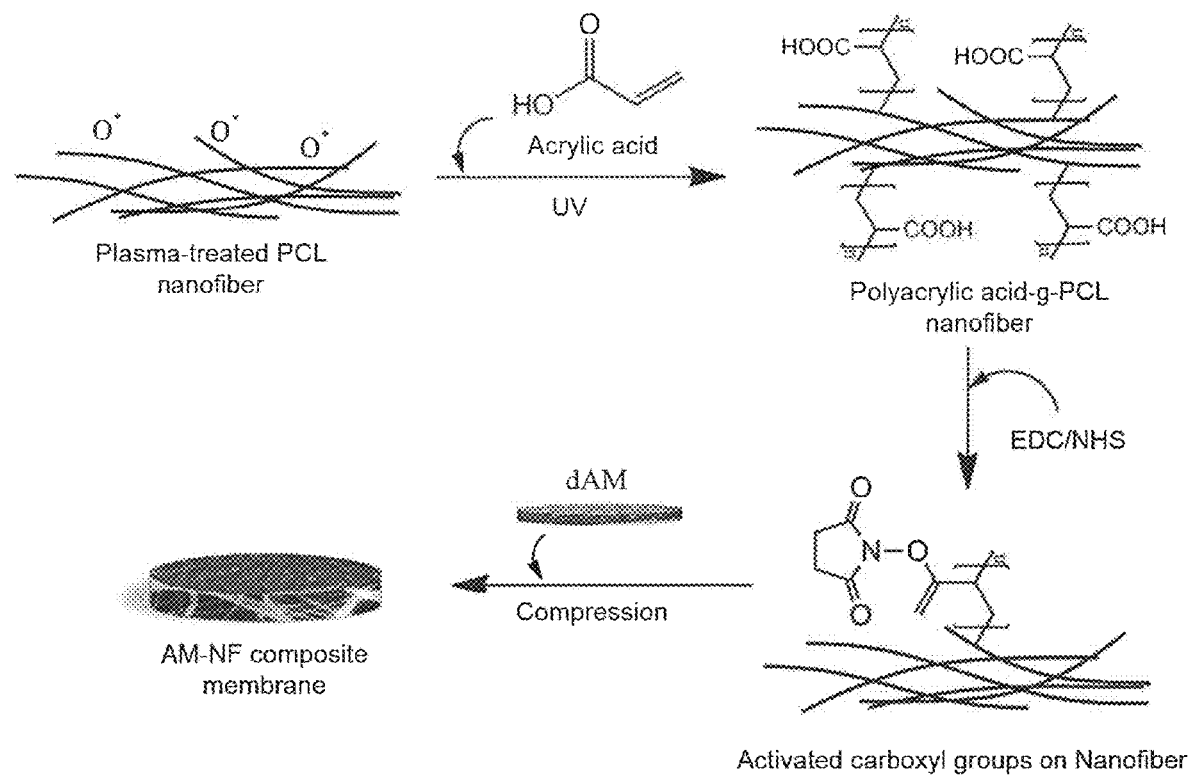
FIG. 1 schematically showed a method for preparation of a composite membrane, comprising: treating a polymer fiber sheet (for example PCL nanofiber membrane) to carry a carboxyl group on the fiber; activating the carboxyl group; compressing the polymer fiber sheet bearing the activated carboxyl group together with a decellularized amniotic membrane to obtain the composite membrane.
Figure 2:
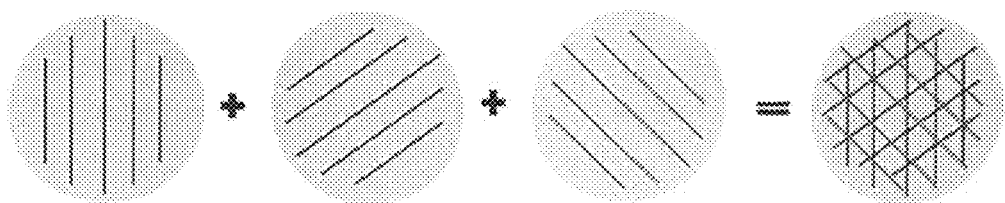
FIG. 2 schematically showed a process of superimposing aligned fiber sheets in which the orientations of the fibers are different among the sheets.

2. Surface treatment of PCL nanofiber membrane: the process was shown in FIG. 1.

1) The PCL nanofiber membrane was treated with a plasma cleaner (Harrick Plasma) at a moderate frequency for 10 minutes to allow the surface of the fiber to carry active oxygen groups.

2) Carboxylation: 10% acrylic acid solution was prepared with deionized water, and sodium periodate ($NaIO_4$) was added, and the final concentration of sodium periodate was 0.5 mM. The plasma treated PCL nanofiber membrane was placed in a clean container, and the container was placed on ice. The solution of 10% acrylic acid-0.5 mM $NaIO_4$ was added to cover the fiber membrane. UV irradiation was performed for 2 minutes (30 to 50 mW/cm$^2$).

3) The UV treated fiber membrane was washed with deionized water for 3 to 5 times, to completely remove the residual reagents. Drying was carried out at room temperature in dark place.

Figure 3:
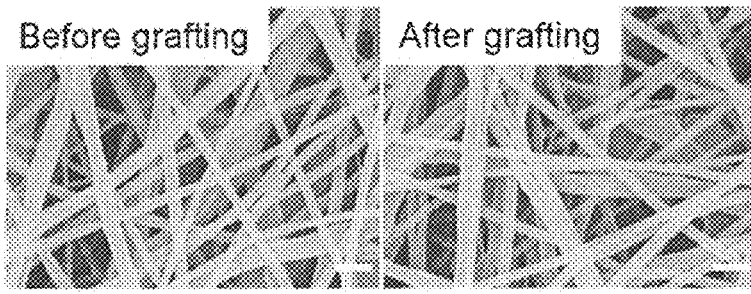
FIG. 3 showed the morphologies of PCL nanofibers before and after carboxylation in Example 1, in which the scale bars were 1 μm. Before and after carboxylation, the fiber surface did not change significantly.
Figure 4:
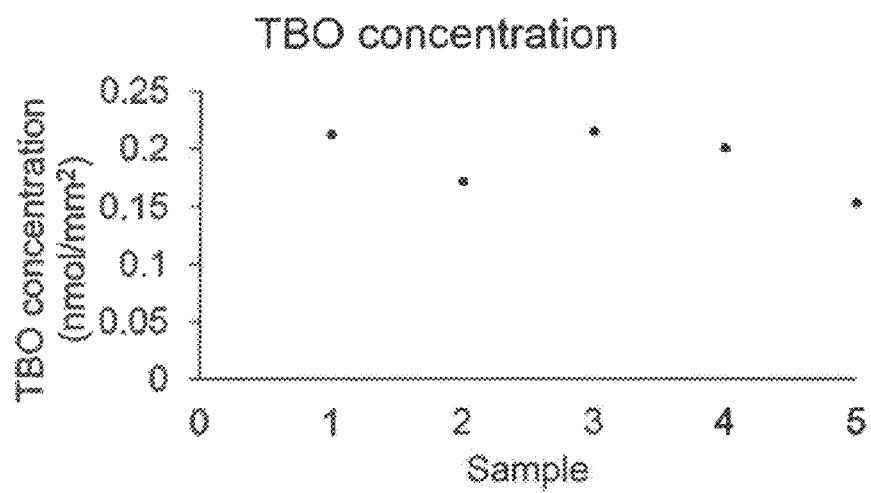
FIG. 4 showed the content of TBO in fiber membrane samples in Example 1.

4) The fiber membrane was observed under a scanning electron microscope before and after carboxylation. As shown in FIG. 3, there was no significant change on the fiber surface before and after carboxylation. The carboxyl group content of the fiber membrane was calculated according to Toluidine Blue O (TBO) reaction. FIG. 4 showed the TBO concentrations in five samples (with thickness of 70 or 80 μm, respectively). As shown in the figure, the average TBO concentration of the fiber membrane was 0.19±0.027 nmol/mm$^2$. The ratio of carboxyl groups to TBO complexes was 1:1. Thus, the carboxyl group concentration of the fiber membrane was about 0.19±0.027 nmol/mm$^2$. The results showed that PCL fiber surface was successfully carboxylated.

5) Activation of the carboxyl group on the surface of die PCL fiber membrane: The masses of NHS and N-(3-dimethylaminopropyl)-N-ethylcarbodiimide (EDC) required for the reaction (molar ratio COOH: NHS/EDC=1:4) were calculated from the carboxyl group content, NHS (Sigma) and EDC (Sigma) in corresponding amounts were weighed and dissolved in 50% ethanol, then added to the carboxylated fiber surface and treated at room temperature in dark place for 5 hours.

6) The fiber membrane vas washed twice with 70% ethanol.

EXAMPLE 2

Decellularization Treatment of Amniotic Membrane

Fresh amniotic membrane was attached to a nitrocellulose membrane, with epithelial side up. A solution of 2.5% Dispase (Millipore) was prepared and dissolved in DMEM/F12 serum-free medium (Life Technology). The amniotic surface was covered with the enzyme solution, treated at 4° C. for 4 hours, and washed with PBS for 3 times. The amniotic membrane was placed in PBS solution and placed under a stereoscope. Epithelial cells were scraped off by using an Iris spatula from left to right, top to bottom. Under the stereoscope, it could be seen that white cell debris fell into PBS solution. The amniotic membrane was washed with PBS solution for 3 times.

Figure 5:
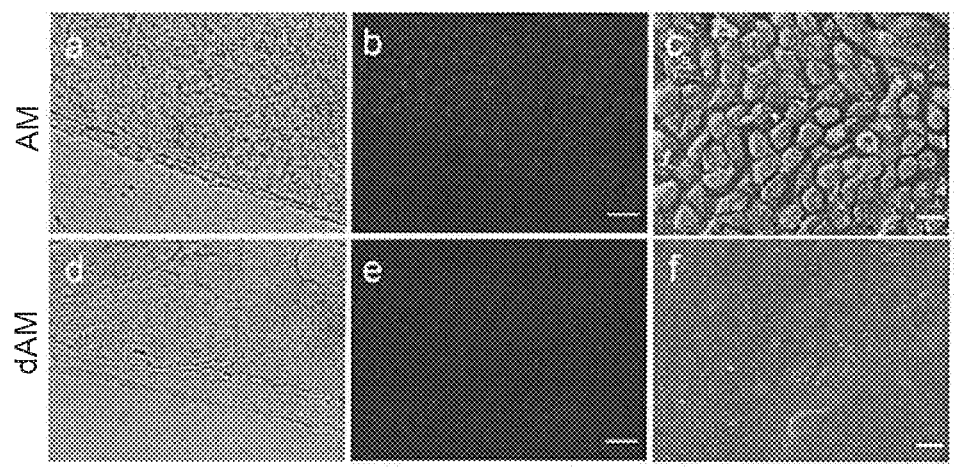
FIG. 5 showed the results of observation of the amniotic membrane with optical microscopes and a scanning electron microscope before and after decellularization (scale bar: 20 μm).

The thickness of the decellularized amniotic membrane was between 20 μm and 40 μm. The amniotic membrane was observed by optical microscope and scanning electron microscope before and after the decellularization, and the results were shown in FIG. 5 (scale bar: 20 μm). FIGS. 5a and 5d showed the surface morphologies of the amniotic membrane observed before and after the decellularization under the optical microscope, respectively. FIGS. 5b and 5c showed the results of observation of the amniotic membrane by a fluorescence microscope before and after the decellularization. The dots in FIG. 5b were DAPI-stained nuclei, and no nucleus was observed in FIG. 5e. FIGS. 5c and 5f showed the surface morphologies of the amniotic membrane observed under the scanning electron microscope before and after decellularization.

As shown in the figures, amniotic epithelial cells were distributed over the entire surface prior to the treatment, while almost no cell remained on the amniotic membrane surface after the treatment, indicating that the amniotic epithelial cells were completely removed.

Figure 6:
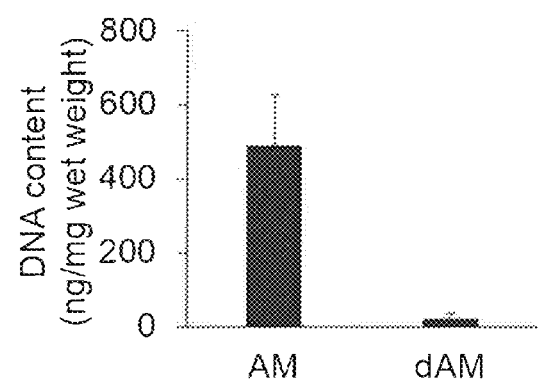
FIG. 6 showed the DNA contents of the amniotic membrane and the decellularized amniotic membrane, respectively. The results showed that the decellularized amniotic membrane contains almost no DNA.

The DNA contents in the amniotic membrane before and after decellularization were detected using the DNA extraction kit (DNeasy® Blood & Tissue Kit, QIAGEN). As shown in FIG. 6, the decellularized amniotic membrane contained almost no DNA.

EXAMPLE 3

Preparation of Decellularized Amniotic Membrane-PCL Nanofiber Composite Membrane ("PCL-dAM Composite Membrane" For Abbreviation)

In an ultra-clean bench, the PCL nanofiber membrane was washed three times with PBS. The decellularized amniotic membrane with epithelial side down and stromal side up was spread out on the surface of Teflon (Polytetrafluoroethene, PTFE) film. The PCL nanofiber membrane was placed on the stromal side of the amniotic membrane. After that, another Teflon film was placed on the nanofiber membrane. The stacked decellularized amniotic membrane, the PCL nanofiber membrane and the Teflon films were placed between two stainless steel plates. The steel plates were placed in a vise, to which a compression of 5 to 7 MP was applied, and stayed at 4° C. for 12 hours. A condensation reaction was carried out between the carboxyl group on the surface of the PCL nanofiber membrane and the amino group on the surface of the decellularized amniotic membrane, and the reaction was more sufficiently performed by compression of the vise. After removal of the steel plates and the Teflon films, the composite membrane was taken out, lyophilized in a freeze dryer (Labconco Freezone 12L Cascade Freeze Dry System), and stored at room temperature.

Figure 7:
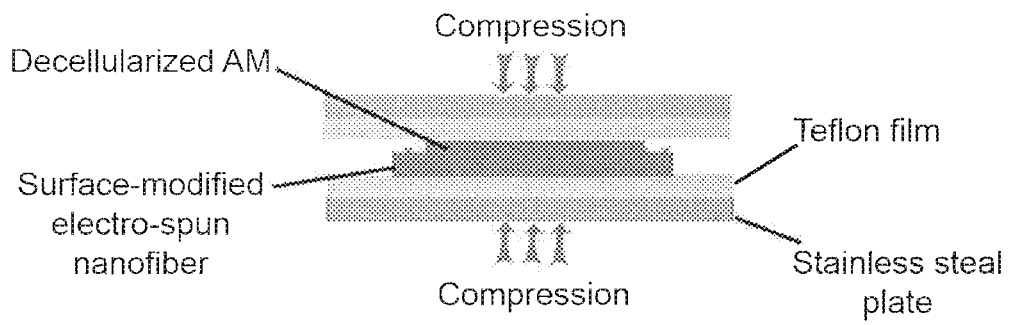
FIG. 7 illustratively showed the composite process and the used apparatus.

FIG. 7 illustratively showed the composite process and the apparatus used therein. In the figure, the decellularized amniotic membrane was laid over the PCL nanofiber membrane with activated carboxyl groups and placed between the two Teflon films; the outer side of each of the two Teflon films had a stainless steel plate, and the stainless steel plates were compressed by the vise, so as to obtain the composite membrane.

The composite membranes with different thicknesses were obtained by using the PCL nanofiber membranes with different thicknesses.

Comparative Example 1: By referring to the process of Example 3, the decellularized amniotic membrane was combined with the PCL nanofiber membrane under the condition without compression.

Comparative Example 2: By referring to the process of Example 1, a PCL nanofiber membrane having a thickness of 80 μm was prepared without treating the membrane surface. By referring to the process of Example 3, this PCL nanofiber membrane was combined with the decellularized amniotic membrane under the condition with compression.

EXAMPLE 4

Preparation of Decellularized Amniotic Membrane-PLA Fiber

Composite Membrane ("PLA-Dam Composite Membrane" for Abbreviation) and Decellularized Amniotic Membrane-PLGA Fiber Composite Membrane ("PLGA-Dam Composite Membrane" for Abbreviation)

1. Preparation of polylactic acid (PEA) fiber membrane: A solution of 9 wt % PEA (PLA, Mw=78 kDa, Mn=48 kDa, Nature Works LLC) was prepared, A certain amount of PLA was weighed and dissolved in a solution of trichloromethane-dimethylformamide at a final concentration of 9%. The PLA solution was added to a syringe and a 27 G syringe needle was mounted. The entire syringe was placed on an electric syringe pump and propelled by using a voltage of 16 kV at an injection speed of 0.5 mL/h. A grounded tin foil paper was used to receive the ejected PLA fibers to form a fiber membrane with a thickness of 80 μm, and the diameter of the fibers was 935 nm (935±218 nm).

2. Preparation of Poly(D,L-lactide-co-glycolide) (PLGA) fiber membrane: 15 wt % polylactic acid-glycolide random copolymer (number ratio of repeating units was: lactic acid: glycolide=50: 50, MW 30 to 60 kDa, Sigma-Aldrich) solution was prepared. A certain amount of PLGA was weighed and dissolved in 1,1,1,3,3,3-hexafluoroisopropanol at a final concentration of 15%. The PLGA solution was added to a syringe and a 27 G needle was mounted. The entire syringe was placed on an electric syringe pump and propelled with a voltage of 6.8 kV at an injection speed of 0.5 mL/h. A grounded tin foil paper was used to receive the ejected PLGA fibers to form a fiber membrane with a thickness of 80 μm, and the diameter of the fibers was 1260 nm (1260±132 nm).

Figure 8:
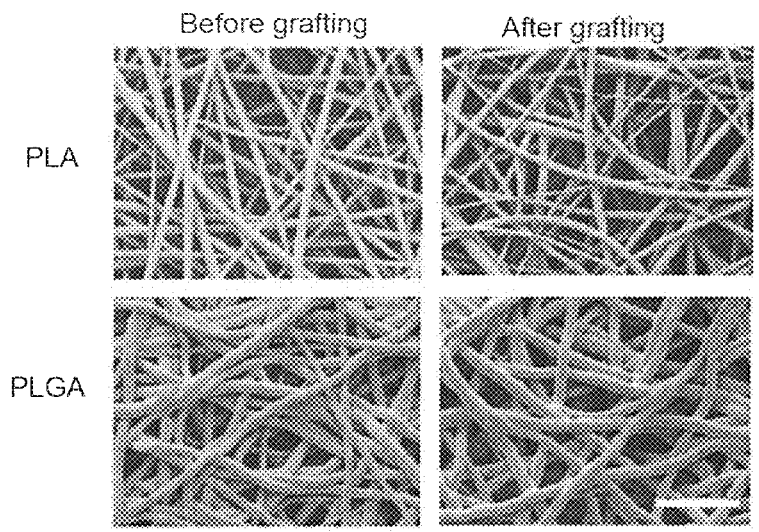
FIG. 8 showed the morphologies of PLA fibers and PLGA fibers before and after carboxylation in Example 4, in which the scale bar was 10 μm. As shown in the figure, there was no significant change in the surfaces of PLA fibers and PLGA fibers before and after carboxylation.

3. The surface treatment process of the PLGA and PLA fiber membranes was similar to that of the PCL fiber membrane. The fiber membranes before and after carboxylation were observed by scanning electron microscope. As shown in FIG. 8, the surface of the PLA and PLGA fibers did not change significantly before and after carboxylation.

Figure 9:
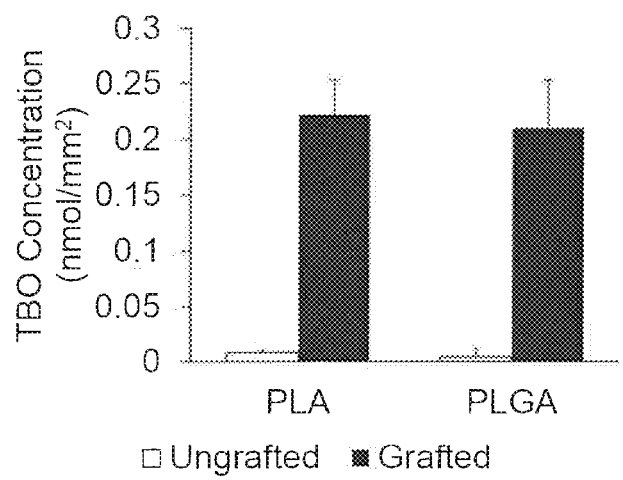
FIG. 9 showed the contents of TBO in the untreated PLA fiber membrane and PLGA fiber membrane, and in the carboxylated PLA fiber membrane and PLGA fiber membrane.

The TBO concentrations of the fiber membranes after carboxylation were detected by TBO assay. The results were shown in FIG. 9, indicating that after carboxylation, the average TBO concentration on the PLA fiber membrane with a thickness of 80 μm was 0.22±0.031 nmol/mm$^2$ and the average TBO concentration on the PLGA fiber membrane with a thickness of 80 μm was 0.21±0.018 nmol/mm$^2$.

EXAMPLE 5

Performance Test of Composite Membranes (1) Stability

Figure 10:
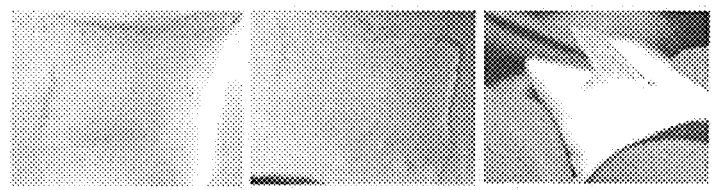
FIG. 10 showed the morphologies of the PCL-dAM composite membranes as prepared in Example 3, Comparative Example 1 and Comparative Example 2 after lyophilization. The results showed that exerting pressure on and treating the surface of the fiber membrane are advantageous for the stable attachment between the nanofiber membrane and the decellularized amniotic membrane.

FIG. 10 showed the morphologies of PCL-dAM composite membranes as prepared in Example 3, Comparative Example 1 and Comparative Example 2 after lyophilization. As shown in the figure, in the composite membrane prepared in Example 3, the decellularized amniotic membrane and the PCL nanofiber membrane were very closely combined together. In the composite membrane prepared under conditions without compression (Comparative Example 1). It could be seen that the decellularized amniotic membrane was detached from the nanofiber membrane at the edge. In the composite membrane prepared with the untreated PCL nanofiber membrane (Comparative Example 2), the decellularized amniotic membrane could be easily peeled off from the untreated PCL nanofiber membrane. The results show that exerting compression on and treating the surface of the fiber membrane were advantageous for the stable attachment between the nanofiber membrane and the decellularized amniotic membrane.

(2) Operability

The operability of the composite membrane was evaluated by observing the state of the composite membrane when it was and clamped with tweezers in a dry and rehydrated states.

Figure 11:
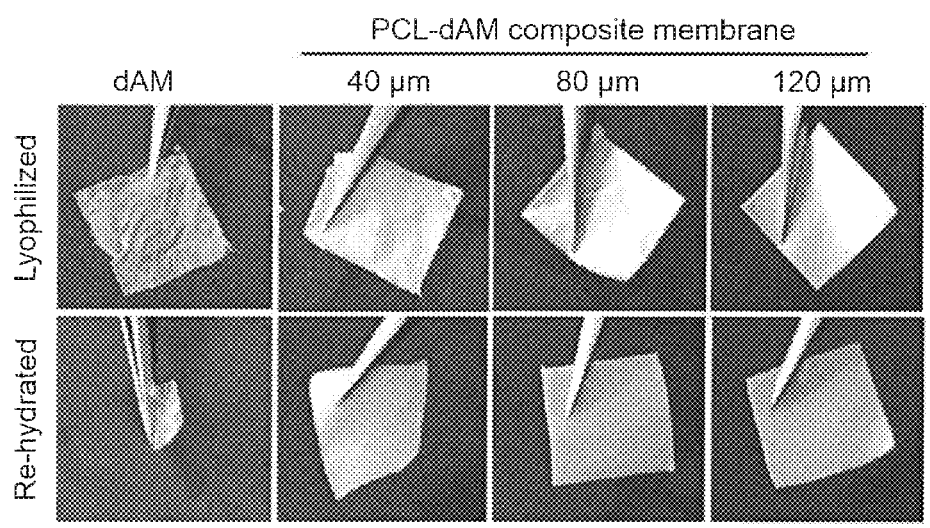
FIG. 11 showed the morphologies of the decellularized amniotic membrane and the PCL-dAM composite membranes with different thicknesses in dry and rehydrated states. As shown in the figure, the decellularized amniotic membranes were adhered together after rehydration and were difficult to unfold, while the composite membranes were easily clamped with tweezers after rehydration and were in stretched state.
Figure 12:
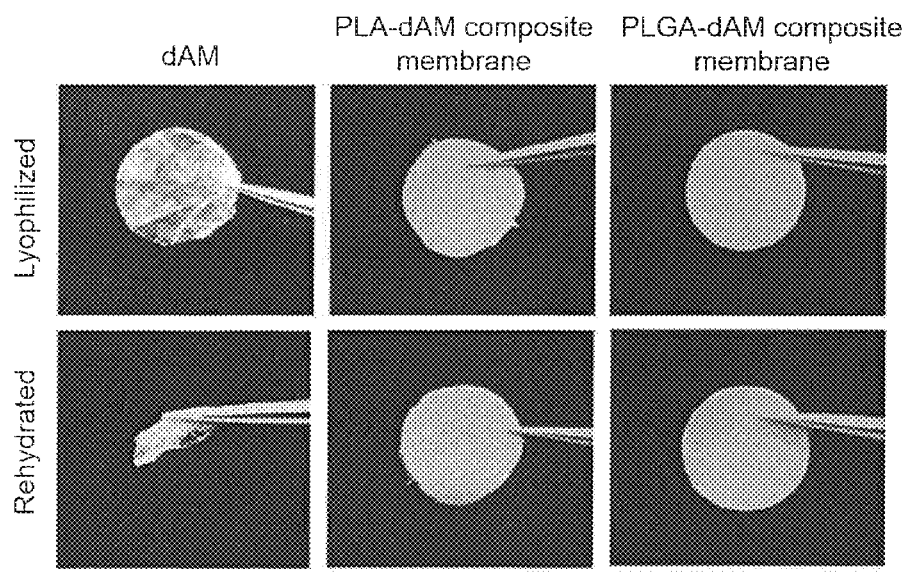
FIG. 12 showed the morphologies of the decellularized amniotic membrane, the PLA-dAM composite membrane, and the PLGA-dAM composite membrane in dry and rehydrated states, in which the thicknesses of said composite membranes were 80 μm. As shown in the figure, the decellularized amniotic membranes were adhered together after rehydration and were difficult to unfold, while the composite membranes were easily clamped with tweezers after rehydration and were in stretched state.

FIG. 11 showed the morphologies of the decellularized amniotic membrane and PCL-dAM composite membranes with different thicknesses in dry and rehydrated states. FIG. 12 showed the morphologies of PLA-dAM composite membrane, and PLEA-dAM composite membrane in dry and rehydrated states. As shown in the figures, the decellularized amniotic membranes were adhered together after rehydration and were difficult to unfold, while the composite membranes were easily clamped with tweezers after rehydration and were in stretched state.

(3) Hydrophilicity

The water contents of the decellularized amniotic membrane, the PCL-dAM composite membranes (thickness: 40 μm, 80 μm, 12.0 μm), the surface-carboxylated and activated PCL nanofiber membrane (thickness: 80 μm) and the untreated PCL nanofiber membrane (thickness: 80 μm) were determined by a process as follows: The freeze-dried membranes were cut, each sample had a size of 1 cm×1 cm, weighed (Wd), and then placed in double distilled water at 37° C. for 10 minutes. The membranes were attached to glass slides, placed vertically for 1 min to drip the surface water, removed from the glass slides and weighed again (Ws).

Figure 13:
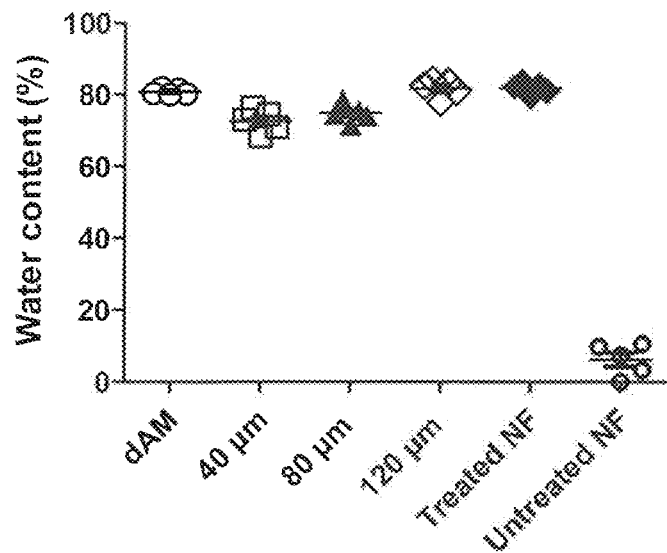
FIG. 13 showed the water contents of the decellularized amniotic membrane, the PCL-dAM composite membranes (thickness: 40 μm, 80 μm, 120 μm), the surface-carboxylated PCL nanofiber membrane (thickness: 80 μm) and the untreated PCL nanofiber membrane (thickness: 80 μm).

Water contents were calculated according to the following formula: Water content (%)=[(Ws−Wd)/Ws]×100. FIG. 13 showed the results. It can be seen from the figure that the composite membrane had a water content similar to those of the decellularized amniotic membrane and the surface-carboxylated PCL nanofiber membrane (Treated NF), and their water contents were about 80%, indicating that the composite membrane exhibited good hydrophilicity during rehydration.

(4) Tensile and Toughness Performance

The stress-strain curves of the decellularized membrane (dAM), as well as PCL-dAM composite membrane, PLA-dAM composite membrane and PLGA-dAM composite membrane which all had a thickness of 40 μm, were measured by the process as follows the membranes after lyophilization were cut to obtain dumbbell-shaped membrane samples, which both ends had a size of 1 cm×1 cm, and the center part had a size of 1 mm×2 mm. The both ends of the I-shaped membrane sample were fixed to metal clamps of a mechanical tester (BOSE Enduratec ELF 3200), the sample was immersed in a phosphate buffer for 2 minutes and then stretched at a rate of 0.5 mm/min. The measurement yielded stress-strain curves, elastic modulus, strain to failure, ultimate tensile strength, and toughness.

Figure 14:
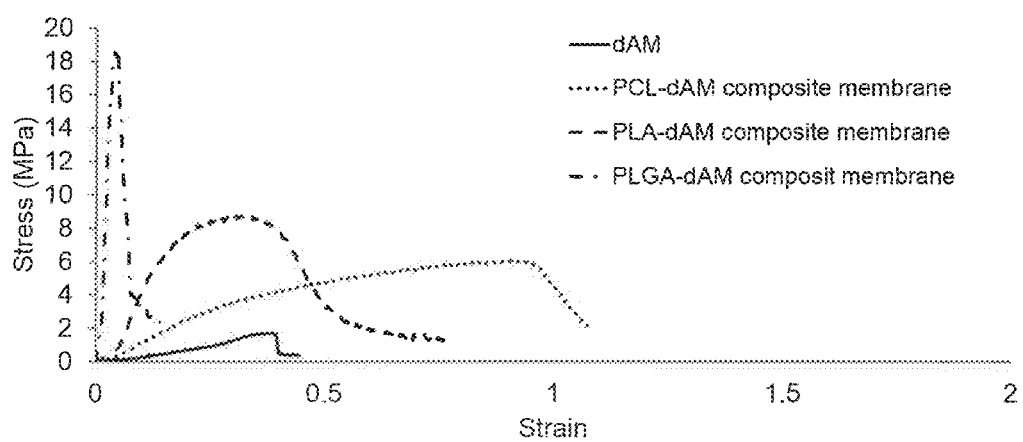
FIG. 14 showed the stress-strain curves of decellularized amniotic membrane, PLGA-dAM composite membrane, PLA-dAM composite membrane and PCL-dAM composite membrane.

The stress-strain curves of the decellularized amniotic membrane and the composite membranes were shown in FIG. 14. The stress-strain curve of PLGA-dAM composite membrane increased and decreased sharply, and exhibited the highest curve peak; the curve of PLA-dAM composite membrane increased and decreased slowly; the curve of PCL-dAM composite membrane increased and decreased more slowly; and the curve of the decellularized amniotic membrane increased slowly, but its curve peak was significantly lower than those of the three composite membranes. These indicate that the decellularized amniotic membrane had good elasticity, but its ultimate tensile strength was the lowest.

Figure 15:
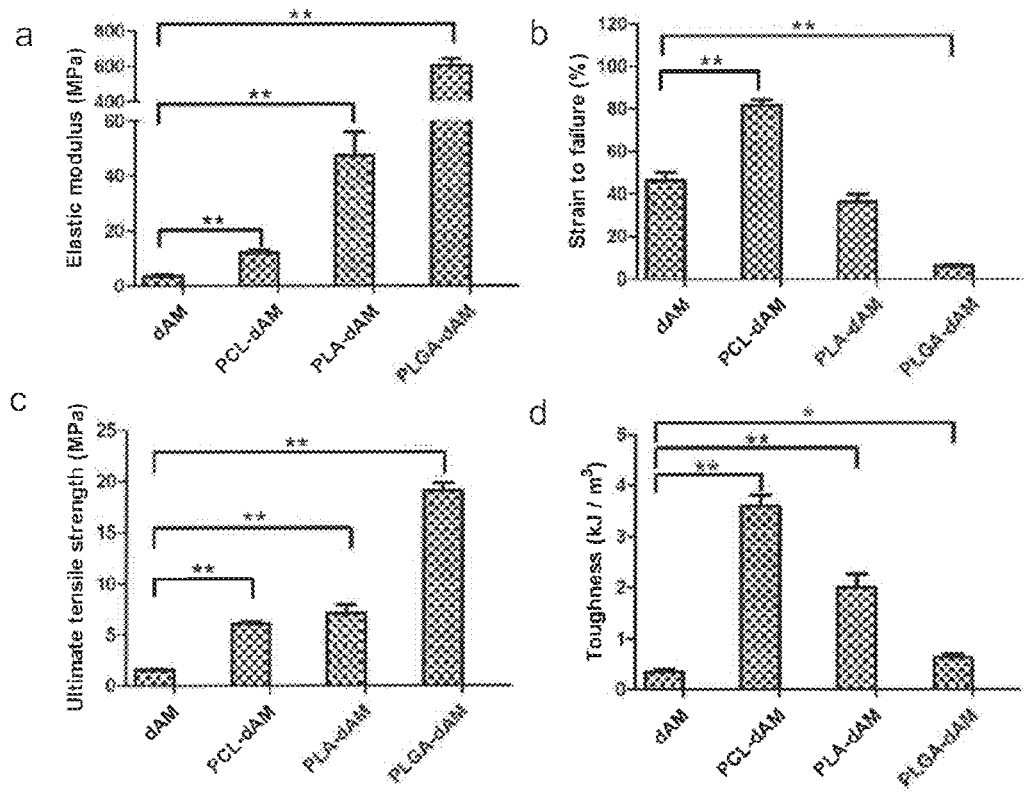
FIG. 15 showed the mechanical test results of decellularized amniotic membrane, PLGA-dAM composite membrane, PLA-dAM composite membrane and PCL-dAM composite membrane: (a) elastic modulus, (b) strain to failure, (c) ultimate tensile strength, and (d) toughness.

FIG. 15 showed the results of other mechanical tests: (a) elastic modulus, (b) strain to failure, (c) ultimate tensile strength, and (d) toughness. As shown in the figures, the decellularized amniotic membrane after rehydration had the lowest elastic modulus compared to the three composite membranes, indicating that its elasticity was best, but its ultimate tensile strength and toughness were the lowest, and significantly lower than those of the three composite membranes, indicating that the tensile properties and toughness of the composite membranes were better than those of the amniotic membrane.

(5) Resistance to Suture Extension

The suture extension test was performed on the decellularized amniotic membrane, PCL-dAM composite membrane with the thickness of 80 μm and untreated PCL nanofiber membrane with the thickness of 80 μm. The procedure was as follows: the membranes after lyophilization were cut to get samples in size of 1 cm×2 cm. One end of the membrane sample was attached to a metal clamp of a mechanical tester (BOSE Enduratec ELF 3200) and the other end was pierced into a 7-0 nylon suture at a distance of 2 mm from the center. A section of the suture was fixed to the metal clamp on the other side. After the membranes were immersed with a phosphate buffer for 2 min, the membranes were stretched at a rate of 0.2 mm/s.

Figure 16:
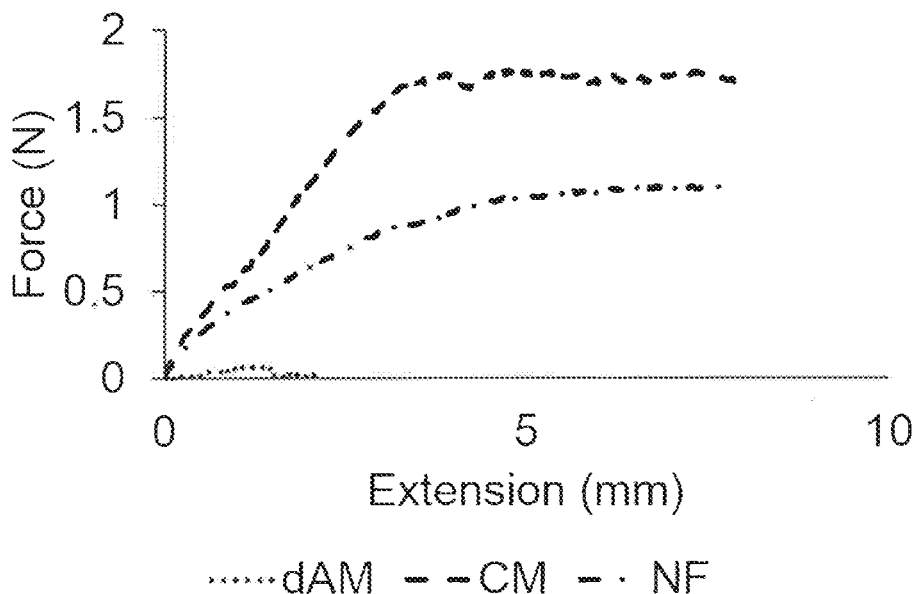
FIG. 16 showed the results of suture extension test for decellularized amniotic membrane (dAM), PCL-dAM composite membrane (CM) with the thickness of 80 μm and untreated PCL nanofiber membrane (NF) with the thickness of 80 μm.

FIG. 16 showed the test results. As shown in the figure, the individual decellularized amniotic membrane was torn apart h the suture when the suture displacement was less than 2 mm. For PCL-dAM composite membrane (CM) and the PCL nanofiber membrane (NF), the pinholes become longer and longer as the suture displacement increased, but these membranes were not torn apart. The results show that the composite membranes were well resistant to suture extension.

EXAMPLE 6

Microtopographic Characterization of PCL-dAM Composite Membrane

Figure 17:
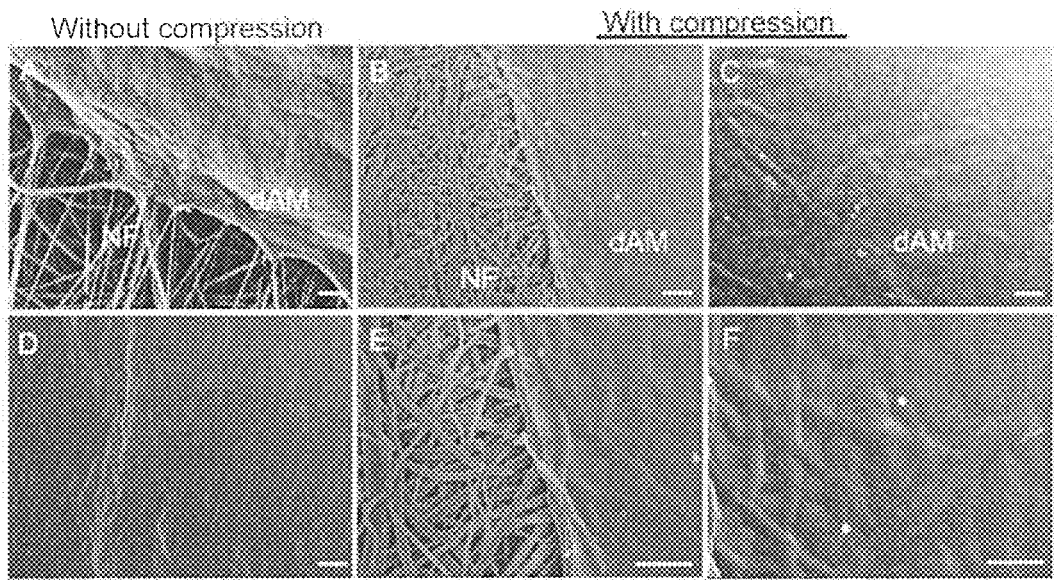
FIG. 17 showed the surface structures of PCL-dAM composite membranes prepared under conditions with and without compression, as observed by scanning electron microscope, and the scale bars were 10 μm. As shown in the figure, in the composite membrane prepared under conditions without compression, the PCL nanofiber membrane (NF) could be bound to the decellularized amniotic membrane by chemical action, but did not exhibit the shape of the PCL, nanofiber on the surface of the decellularized amniotic membrane (FIGS. 17A, 17D), indicating that the combination between the decellularized amniotic membrane and PCL nanofiber membrane was weak. In the composite membrane prepared under conditions with compression, the morphology of the PCL nanofiber was clearly visible on the surface of the decellularized amniotic membrane (FIG. 17B, C, E, F), indicating that the decellularized amniotic membrane and PCL nanofiber membrane were tightly combined and formed an integrated composite structure.

FIG. 17 showed the surface structures of PCL-dAM composite membranes prepared under conditions with and without composition, as observed by a scanning electron microscope. The scale bars were 10 μm. As shown in the figure, in composite membrane prepared without compression, the PCL nanofiber membrane (NE) could be combined with the decellularized amniotic membrane by chemical action, but the morphology of the PCL nanofiber did not present on the surface of the decellularized amniotic membrane (FIGS. 17A, 17D), indicating that the combination between the decellularized amniotic membrane and the PCL nanofiber membrane was relatively weak. In the composite membrane prepared with compression, the morphology of the nanofiber was clearly visible on the surface of the decellularized amniotic membrane (FIGS. 17B, C, E, F), indicating that the decellularized amniotic membrane and the PCL nanofiber membrane were tightly connected and formed an integrated composite structure.

Figure 18:
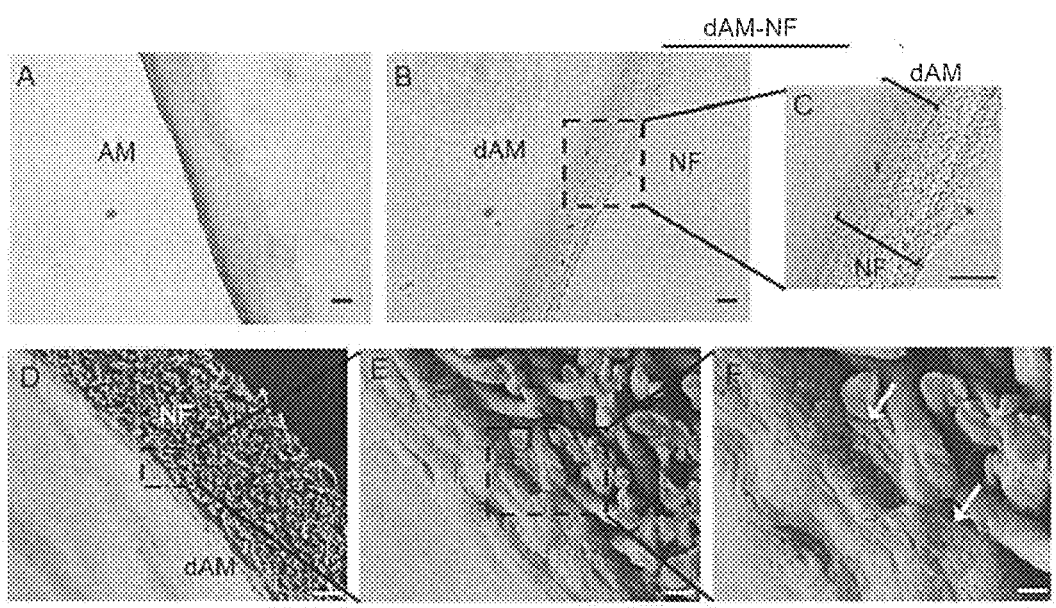
FIG. 18 showed the cross-section of the natural amniotic membrane and PCL-dAM composite membrane.

FIG. 18 showed the cross-section of the natural amniotic membrane and PCL-dAM composite membrane. FIGS. 18A-18C showed optical micrographs of the cross-section after H&E staining, with a scale bar of 20 μm. FIG. 18A showed that the natural amniotic membrane composed of a layer of epithelial cells and a sponge-like stromal structure. FIGS. 18B and 18C showed that, as observed on the cross-section of the composite membrane, the PCL nanofiber membrane (NF) had been merged into the stroma of the decellularized amniotic membrane, and the decellularized amniotic membrane and the PCL nanofiber membrane were overlapped. FIGS. 18D to 18F showed scanning electron micrographs of the cross-section, in which FIGS. 18D, 18E and 18F had a scale bar of 10 μm, 2 μm and 1 μm, respectively. The ultra-microstructure of the composite membrane showed that the PCL nanofiber membrane connected to the decellularized amniotic membrane very closely (FIGS. 18E, 18F). The results show that the PCL nanofiber membrane and the decellularized amniotic membrane successfully form a composite membrane through physical and chemical interactions.

EXAMPLE 7

Figure 19:
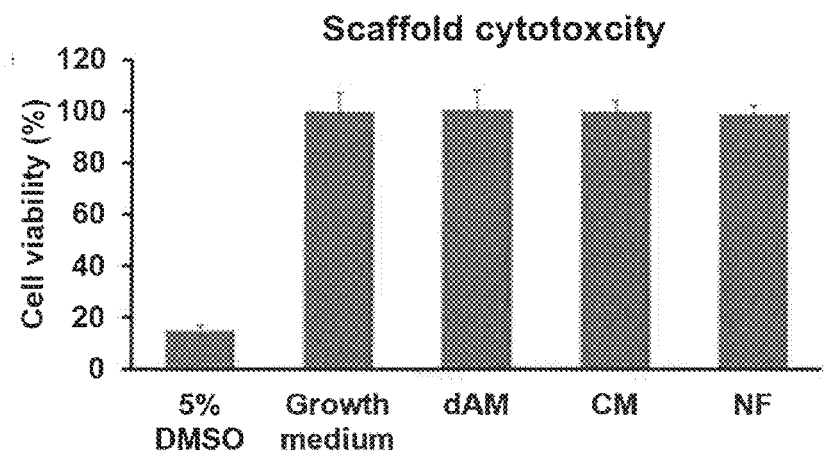
FIG. 19 showed the survival rates of corneal fibroblasts on the decellularized amniotic membrane (dAM), PCL-dAM composite membrane (CM) and the PCL nanofiber membrane (NF). The results showed that none of the decellularized amniotic membrane, PCL-dAM composite membranes or the PCL nanofiber membrane had cytotoxicity.

Evaluation of the Safety of the Composite Membrane and its Effect on Cell Morphology and Proliferation (1) Safety Test The decellularized amniotic membrane, the PCL-dAM composite membrane prepared in Example 3 and the PCL nanofiber membrane, were cut into a size of 1 cm×1 cm, and each of them was immersed into 200 μL of E12/DMEM low-glucose medium (containing 10% FBS and 1% penicillins/streptomycin) for 48 hours to obtain a leachate of membrane material. Corneal fibroblasts were implanted into a 96-well plate at an amount of $10^3$ cells per well and cultured for 24 hours. The cell culture medium was replaced with the membrane leachate, or fresh medium (positive control), or 5% DMSO (negative control). After 72 hours of incubation, the medium was discarded and 10% alamar Blue® (Invitrogen) reaction solution was added, and incubated in a 5% $CO_2$, 37° C. incubator for 2 hours. Absorbance was detected at 570 nm. FIG. 19 showed the survival rate of each group of cells. The results showed that none of the decellularized amniotic membrane (dAM), PCL-dAM composite membrane (CM) or the PCL nanofiber membrane (NF) has cytotoxicity.

(2) Cell Morphology Detection

Corneal fibroblasts were implanted on the decellularized amniotic membrane, PCL-dAM composite membrane prepared in Example 3, the PCL nanofiber membrane, and the Tissue Culture Polystyrene (TCPS) cell culture plate, and cultured with serum-free medium or 10% serum medium. After 7 days of incubation, the cells were fixed with 4% paraformaldehyde for 10 min. After being washed with phosphate buffer, treatment with 0.1% Triton X-100 was carried out for 5 min. After being washed with phosphate buffer, Fluorescent Phallotoxins was added to the solution (Alexa Fluor® 546 Phalloidin, Invitrogen), and incubation was performed at room temperature for 20 min. After being washed with phosphate buffer, DAPI dye liquor (Invitrogen) was added and incubation was performed at room temperature for 10 min. After being washed with phosphate buffer, the cells were sealed for observation.

Figure 20:
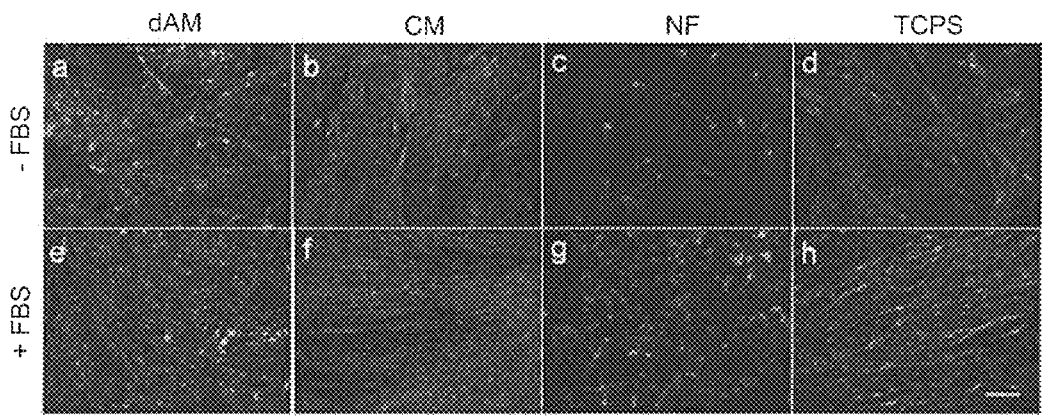
FIG. 20 showed the morphologies of corneal fibroblasts after 7 days of culture under conditions with and without serum on the decellularized amniotic membrane (dAM), the PCL-dAM composite membrane (CM), the PCL nanofiber membrane (NF) and the TCPS tissue culture polystyrene (TCPS), in which the scale bar was 50 μm. As shown in the figure, the cells showed a conventional spindle shape on the decellularized amniotic membrane, the PCL-dAM composite membrane and the cell culture plate in the serum-free medium, whereas the cells were hardly stretched on the PCL nanofiber membrane. In the serum-containing medium, the cells grew and covered the decellularized amniotic membrane, the PCL-dAM composite membrane and the cell culture plate, and formed cell layers. On the PC, fiber membrane, the cells did not form a cell layer. This result showed that similar to the decellularized amniotic membrane, the composite membrane of the present invention provided a suitable attachment surface for cell growth, which facilitates the adhesion, stretching and growth of cells.

FIG. 20 showed the morphologies of corneal fibroblasts after 7 days of culture under conditions with and without serum on the decellularized amniotic membrane (dAM), the PCL-dAM composite membrane (CM), the PCL nanofiber membrane (NF) and the TCPS cell culture plate (TCPS), in which the scale bar was 50 μm. As shown in the FIG. 20, the cells showed a conventional spindle shape on the decellularized amniotic membrane, the PCL-dAM composite membrane and the cell culture plate in the serum-tree medium, whereas the cells were hardly stretched on the PCL nanofiber membrane. In the serum-containing medium, the cells grew and covered the decellularized amniotic membrane, the PCL-dAM composite membrane and the cell culture plate, and formed cell layers. On the PCL fiber membrane, the cells did not form a cell layer. This result shows that similar to the decellularized amniotic membrane, the composite membrane of the present invention provides a suitable attachment surface for cell growth, which facilitates the adhesion, stretching and growth of the cells.

(3) Cell Proliferation Test

The proliferation of cells on the decellularized amniotic membrane, the PCL-dAM composite membrane prepared in Example 3, the PCL nanofiber membrane, and the TCPS cell culture plate under serum-free culture conditions was studied. The process was as follows:

CellCrown™ insert was purchased from Sigma. The membrane was placed between the cylindrical holder and the round sleeve chuck of the CellCrown™ insert to form a cylindric membrane support. Cells were grown on different membrane supports at a density of $5×10^3$ cells/$cm^2$ under serum-free culture conditions. The activity of the cells was examined at the $1^{st}$, $3^{rd}$, $5^{th}$, and $7^{th}$ day, respectively. The medium was discarded and 10% alamar Blue® (lnvitrogen) reaction solution was added, Incubation was performed in a 5% $CO_2$, 37° C. incubator for 2 hours. Absorbance was detected at 570 nm.

Figure 21:
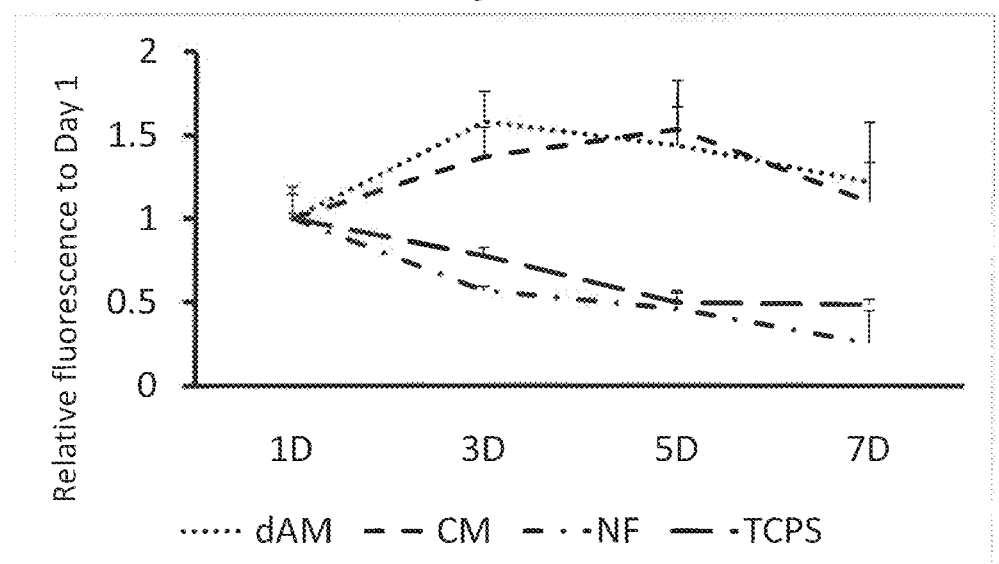
FIG. 21 showed the proliferation of cells on the decellularized amniotic membrane (dAM), the PCL composite membrane (CM), the PCL nanofiber membrane (NF) and the TCPS cell culture plate (TCPS) under serum-free culture conditions. All fluorescence detection values were compared to the values detected on the first day. The results showed that the composite membrane of the present invention well retained the nutrients in amniotic membrane and provided the nutrients for cell growth.

FIG. 21 showed the proliferation of cells on different membranes under serum-free culture conditions. All fluorescence detection values were compared to the values detected on the first day. As shown in the figure, the cell viability gradually decreased on the PCL nanofiber membrane (NF) and the TCPS cell culture plate (TCPS) from the $1^{st}$ day to the $7^{th}$ day under serurn-free culture conditions. However, the cell viability increased from the $1^{st}$ day to the $3^{rd}$ day when the cells were cultured on the surface of the decellularized amniotic membrane (dAM), began to decline 3 days later. On the PCL-dAM composite membrane (CM), the situation was similar to that of the amniotic membrane, i.e., the cell viability increased from the $1^{st}$ day 1 to the $5^{th}$ day, decreased from the $5^{th}$ day, and there was no net growth from the $7^{th}$ day. This suggests that the composite membrane of the present invention retains well the nutrients in the amniotic membrane and provides nutrients for cell growth.

EXAMPLE 8

Evaluation of the Anti-Inflammatory Effects of the Composite Membrane

Furthermore, the anti-inflammatory effects of the composite membrane was evaluated to examine whether the composite membrane had the effect of promoting macrophage to transit from M1 type to M2 type, as the amniotic membrane. The procedure was as follows:

The macrophages derived from mouse bone marrow mesenchymal cells were first isolated and cultured, then the macrophages were grown on the decellularized amniotic membrane, the PCL-dAM composite membranes prepared in Example 3, the PCL nanofiber membrane and TCPS cell culture plate, and inflammatory stimulating factors (LPS and IFN-γ) were added. After 48 hours, real-time Q-PCR was used to detect the expression of markers of M1 and M2.

Figure 22:
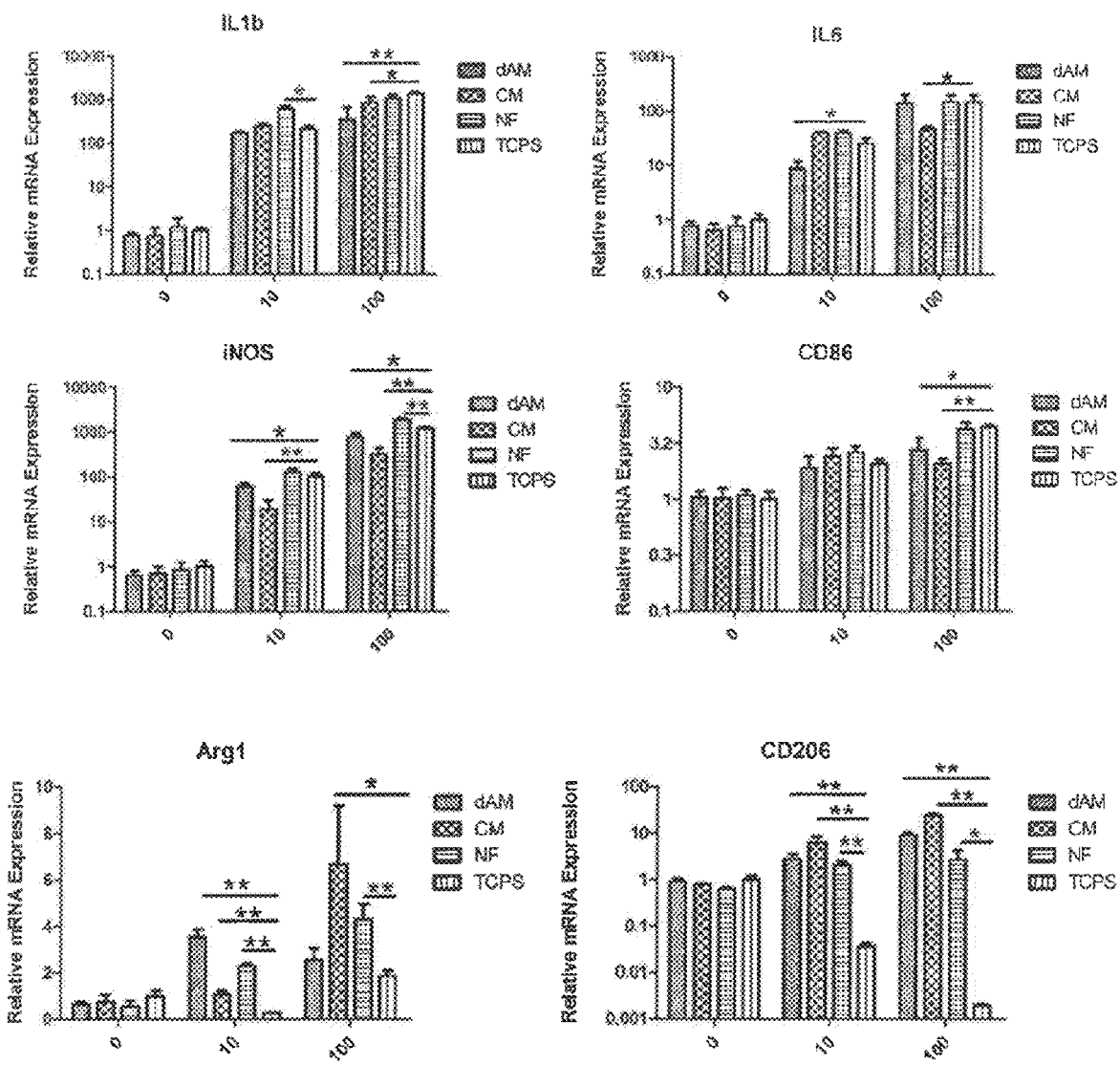
FIG. 22 showed the expression of markers of M1 type macrophage and M2 type macrophage after culturing for 48 hours the mouse bone marrow-derived macrophages that were implanted on the decellularized amniotic membrane (dAM), the PCL-dAM composite membrane (CM), the PC, nanofiber membrane (NF), and the TCPS tissue culture polystyrene (TCPS) with inflammatory stimulating factors with different concentrations. The results represented mean±SD (n=3). *$P<0.05$, **$P<0.01$. The results showed that the composite membrane of the present invention had anti-inflammatory properties similar to that of amniotic membrane, which can promote the transformation of macrophages from pro-inflammatory type to anti-inflammatory type.

FIG. 22 showed the expression of markers of M1 type macrophage and M2 type macrophage after culturing for 48 hours the mouse bone marrow-derived macrophages that were implanted on the decellularized amniotic membrane (dAM), the PCL-dAM composite membrane (CM), the PCL nanofiber membrane (NE), and TCPS cell culture plate (TCPS) with inflammatory stimulating factors with different concentrations. As shown in the figure, the markers of M1 and M2 had similar expression on different substrates when no stimulatory factor was added (LPS: 0 ng/ml; IFNγ: 0 ng/ml). After the stimulating factors LPS and IFNγ were added, the expression of M1 markers (IL1b, IL6, iNOS and CD86) increased with the increase of concentration of the stimulating factors, while the expression of M2 marker CD206 gradually decreased.

The expression of M1 marker iNOS in the cells cultured on the decellularized amniotic membrane and the composite membrane in the presence of low concentration of stimulating factors decreased significantly in comparison with the cells cultured on TCPS. In the presence of high concentration of stimulating factors, the expression of M1 markers IL1b, iNOS and CD86 all decreased significantly. The expression of M2 markers Arg1 and CD206 all increased significantly in the cells cultured on the decellularized amniotic membrane and the composite membrane in the presence of either lower or higher concentration of stimulating factors, in comparison with the cells cultured on the cell culture plate. Hence, in the inflammatory environment, the decellularized amniotic membrane and the PCL-dAM composite membrane could significantly reduce the expression of proinflammatory factors, improve the expression of anti-inflammatory factors. This suggests that the composite membrane of the present invention has anti-inflammatory properties similar to that of amniotic membrane, and can promote the transformation of macrophages from proinflammatory type to anti-inflammatory type.

EXAMPLE 9

Obtaining an Aligned Electrospun Hydrogel Fiber Membrane and Preparation of an Decellularized Amniotic Membrane-Collagen Composite Membrane ("Collagen-dAM" for Abbreviation)

Similar to the PCL fiber membrane, a hydrogel electrospun fiber membrane (such as electrospun collagen fiber membrane) could also form a composite membrane with the decellularized amniotic membrane. The gelling material was dissolved in a water-soluble solution and then electrospun, in which a cross-linking agent was added for crosslinking.

Collagen was taken as an example. First, 1% (wt %) solution of collagen (Elastin Products Company) was prepared. A certain amount of collagen was weighed and dissolved in 75 mM citric acid solution (pH=3.7). The collagen solution was added to a syringe and a 27 G needle was mounted. The entire syringe was placed on a motor-driven syringe pump, and the electrospun fibers were sprayed into a disc collection device containing 50 mg/mL of EDC cross-linker. EDC could quickly cross-link the amino groups and carboxyl groups distributed in the collagen to further form microfibers. The disc collection device had a rotational speed of 50 RPM. The electric syringe pump was moved on an electric translation stage to obtain an aligned fiber membrane with a width of 2 cm. The collected hydrogel fiber membrane was dehydrated by dehydration reagent (for example ethanol) with gradient concentrations (0 to 100%).

Figure 23:
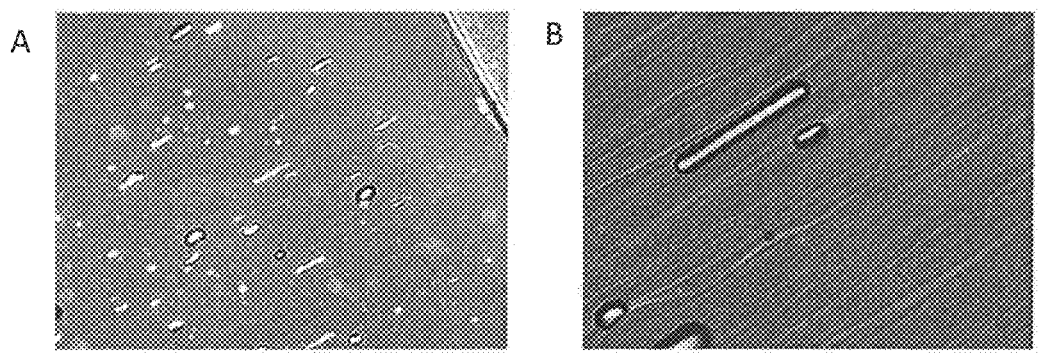
FIG. 23 showed the surface morphology of EDC crosslinked aligned collagen fibers, FIG. 23A showed an image magnified 25 times, and FIG. 23B showed an image magnified 100 times. As shown in these figures, the collagen fibers were regular and arranged in parallel.

FIG. 23 showed the surface morphology of EDC cross-linked aligned collagen fibers, FIG. 23A showed an image magnified 25 times, and FIG. 23B showed an image magnified 100 times. As shown in these figures, the collagen fibers are regular and arranged in parallel.

The dehydrated collagen fiber membrane was treated with 50 mM EDC/NHS at room temperature for 2 hours, and afterwards, washed thoroughly with PBS. The decellularized amniotic membrane with epithelial side up and stromal side down was spread out on a Teflon film. The collagen fiber membrane was placed on the stromal side of the decellularized amniotic membrane. Another Teflon film was placed on the collagen fiber membrane. The entire composition was placed between two steel plates. The steel plates were placed in the jaws of a vise. The claw beam of the vise was turned to exert a compression of 1 MP. After standing and reacting at VC for 12 hours, the steel plates and the Teflon films were removed, and the composite membrane was freeze dried under vacuum.

EAMPLE 10

Test for Transparency of the Collagen-dAM Composite Membrane

Figure 24:
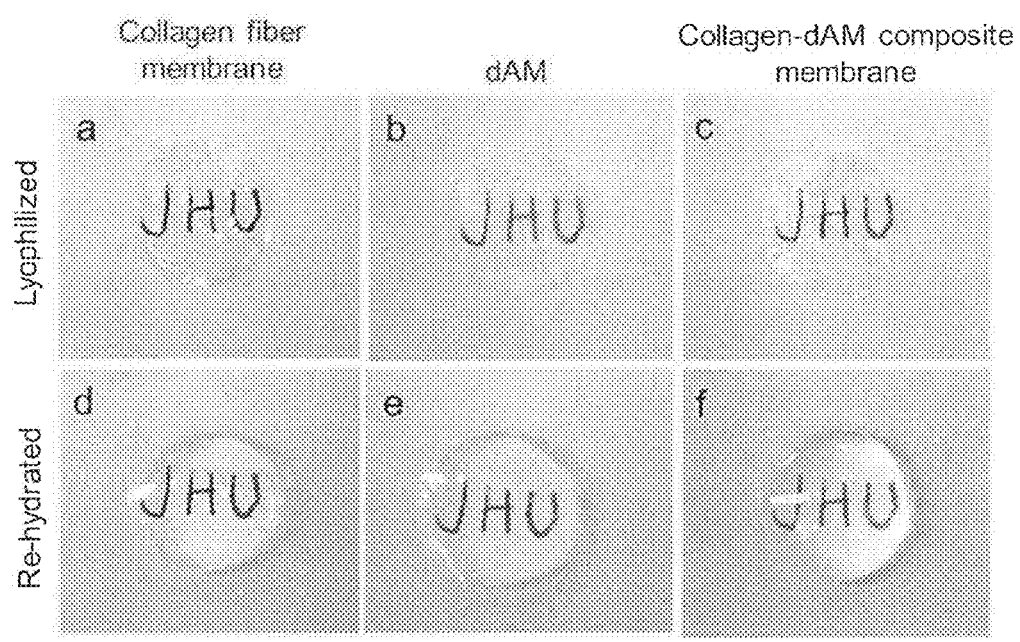
FIG. 24 showed the transparencies of the collagen fiber membrane, the decellularized amniotic membrane and the collagen-dAM composite membrane, in which the membranes had a diameter of 8 mm. As shown in the figure, the letters "JHU" under the three membranes were clearly visible in both dry and rehydration conditions. The transparency of the collagen fiber membrane was even slightly higher than that of the amniotic membrane.

The transparencies of the collagen fiber membrane, the decellularized amniotic membrane and the collagen-dAM composite membrane were measured. As shown in FIG. 24, the letters "JHU" under the three membranes were clearly visible in both dry and rehydrated states. The transparency of the collagen fiber membrane was even slightly stronger than that of the amniotic membrane. This suggests that the collagen fiber membrane played a role as physical support to the decellularized amniotic membrane, and does not weaken the transparency of the amniotic membrane.

While the specific embodiments of the present invention have been described in detail, those skilled in the art will appreciate that various modifications and variations of the details may be made in accordance with all teachings already disclosed and that such changes are within the scope of the present invention. The entire scope of the invention is given by the appended claims and any equivalents thereof.

What is claimed is:

1. A composite membrane, comprising at least one decellularized amniotic membrane and at least one fibrous layer comprising polymer fibers, wherein the at least one fibrous layer is attached to the at least one decellularized amniotic membrane through a chemical bond: wherein the chemical bond comprises amide bonds or ester bonds.

2. The composite membrane according to claim 1, wherein the polymer fibers comprise a polymer having biocompatibility or biodegradability.

3. The composite membrane according to claim 1, wherein the polymer fibers in the at least one fibrous layer are randomly oriented, or oriented substantially in parallel to one another wherein an angle formed by any two fibers is from 0° to 10°.

4. The composite membrane according to claim 1, wherein the composite membrane has at least one of the following features:
(a) the composite membrane has a strain to failure of 5% to 200%;
(b) the composite membrane has an elastic modulus of 0.2 MPa to 1000 MPa; and
(c) the composite membrane has a toughness of 0.5 MJ/m$^3$ to 50 MJ/m$^3$.

5. A method for preparing a composite membrane according to claim 1, comprising the steps of:
(a) obtaining or having obtained the at least one decellularized amniotic membrane;
(b) obtaining or having obtained the at least one fibrous layer, wherein the at least one fibrous layer comprises a polymer fiber sheet, wherein at least one surface of the polymer fiber sheet has a reactive group; and
(c) fitting the surface of the polymer fiber sheet that has the reactive group to the decellularized amniotic membrane.

6. The method according to claim 5, wherein the decellularized amniotic membrane in step (a) is selected from (i) a de-epithelialized amniotic membrane and (ii) a fully decellularized amniotic membrane.

7. The method according to claim 5, wherein the polymer fiber sheet in step (b) is a nonwoven fiber sheet.

8. The method according to claim 5, wherein the polymer fiber sheet in step (b) is made of a polymer having biocompatibility or biodegradability.

9. The method according to claim 5, wherein step (c) comprises fitting the surface of the polymer fiber sheet that has the reactive group to the stromal side of the decellularized amniotic membrane.

10. The method according to claim 5, wherein step (c) is carried out at a temperature of 4 to 25° C.

11. An article, comprising the composite membrane according to claim 1.

12. A method for repairing a damaged soft tissue of a subject, comprising administering the composite membrane according to claim 1 or an article comprising the composite membrane according to claim 1 to the damaged soft tissue of the subject.

13. A method for treatment of an ophthalmic disease in a subject, comprising administering the composite membrane according to claim 1 or an article comprising the composite membrane according to claim 1 to an affected part in an ocular region of the subject.

14. The composite membrane according to claim 1, wherein the at least one fibrous layer is attached to a stromal side of the at least one decellularized amniotic membrane.

15. The composite membrane according to claim 1, wherein the at least one fibrous layer is a nanofiber layer or a microfiber layer.

16. The composite membrane according to claim 1, wherein the polymer fibers comprise a polymer selected from the group consisting of an aliphatic polyester, a polyester ether, a polyphosphazene, a polycarbonate, a polyamino acid, a collagen, a fibrin, a chitosan, an alginate, a hyaluronic acid, a fibronectin, a gelatin, a dextran, an elastin, a polylactic acid (PLA), a polyglycolide (PGA), a poly(D,L-lactide-co-glycolide) (PLGA), a polycaprolactone (PCL), and any combination thereof.

17. The composite membrane according to claim 1, wherein the at least one decellularized amniotic membrane is selected from (i) a de-epithelialized amniotic membrane, and (ii) a fully decellularized amniotic membrane.

18. The composite membrane according to claim 1, wherein the at least one fibrous layer is a hydrogel.

19. The composite membrane according to claim 1, wherein the at least one fibrous layer is attached directly to the decellularized amniotic membrane.

* * * * *